(12) United States Patent
Domb et al.

(10) Patent No.: US 7,732,404 B2
(45) Date of Patent: *Jun. 8, 2010

(54) PRO-NANODISPERSION FOR THE DELIVERY OF CYCLOSPORIN

(75) Inventors: Abraham J. Domb, Efrat (IL); Avi Avramoff, Haifa (IL); Victor Pevzner, Hadera (IL)

(73) Assignee: Dexcel Ltd, Hadera (IL)

( * ) Notice: Subject to any disclaimer, the term of this patent is extended or adjusted under 35 U.S.C. 154(b) by 235 days.

This patent is subject to a terminal disclaimer.

(21) Appl. No.: 11/363,379

(22) Filed: Feb. 28, 2006

(65) Prior Publication Data

US 2006/0205639 A1 Sep. 14, 2006

Related U.S. Application Data

(63) Continuation-in-part of application No. 09/869,519, filed as application No. PCT/IL99/00710 on Dec. 30, 1999, now Pat. No. 7,026,290.

(51) Int. Cl.
*A61K 38/13* (2006.01)
(52) U.S. Cl. .......................................... 514/11; 514/9
(58) Field of Classification Search ........................ None
See application file for complete search history.

(56) References Cited

U.S. PATENT DOCUMENTS

| | | | |
|---|---|---|---|
| 3,288,824 A | 11/1966 | Mahler et al. |
| 3,813,345 A | 5/1974 | Urton |
| 3,954,967 A | 5/1976 | Urton |
| 4,073,943 A | 2/1978 | Wretlind et al. |
| 4,117,118 A | 9/1978 | Härri et al. |
| 4,146,499 A | 3/1979 | Rosano |
| 4,156,719 A | 5/1979 | Sezaki et al. |
| 4,215,199 A | 7/1980 | Härri et al. |
| 4,337,993 A | 7/1982 | Kompfner |
| 4,388,307 A | 6/1983 | Cavanak |
| 4,567,161 A | 1/1986 | Posanski et al. |
| 4,572,915 A | 2/1986 | Crooks |
| 4,695,450 A | 9/1987 | Bauer et al. |
| 4,713,246 A | 12/1987 | Begum et al. |
| 4,719,239 A | 1/1988 | Muller et al. |
| 4,727,109 A | 2/1988 | Schmidt et al. |
| 4,731,384 A | 3/1988 | Dell et al. |
| 4,753,963 A | 6/1988 | Jandacek et al. |
| 4,794,000 A | 12/1988 | Ecanow |
| 4,797,272 A | 1/1989 | Linn et al. |
| 4,797,273 A | 1/1989 | Linn et al. |
| 4,798,823 A | 1/1989 | Witzel |
| 4,835,002 A | 5/1989 | Wolf et al. |
| 4,861,580 A | 8/1989 | Janoff et al. |
| 4,871,768 A | 10/1989 | Bistrian et al. |
| 4,885,172 A | 12/1989 | Bally et al. |
| 4,888,239 A | 12/1989 | Brox |
| 4,904,474 A | 2/1990 | Theeuwes |
| 4,944,949 A | 7/1990 | Story et al. |
| 4,963,362 A | 10/1990 | Rahman et al. |
| 4,963,367 A | 10/1990 | Ecanow |
| 4,970,076 A | 11/1990 | Horrobin |
| 4,990,337 A | 2/1991 | Kurihara et al. |
| 4,994,439 A | 2/1991 | Longenecker et al. |
| 4,996,193 A | 2/1991 | Hewitt et al. |
| 5,037,653 A | 8/1991 | Dawson |
| 5,041,278 A | 8/1991 | Janoff et al. |
| 5,047,396 A | 9/1991 | Orbán et al. |
| 5,051,402 A | 9/1991 | Kurihara et al. |
| 5,071,643 A | 12/1991 | Yu et al. |
| 5,081,105 A | 1/1992 | Bistrian |
| 5,120,710 A | 6/1992 | Liedtke |
| 5,145,684 A | 9/1992 | Liversidge et al. |
| 5,154,754 A | 10/1992 | Damó et al. |
| 5,154,930 A | 10/1992 | Popescu et al. |
| 5,156,960 A | 10/1992 | Jekkel née Bokány et al. |
| 5,171,578 A | 12/1992 | Bally |
| 5,188,837 A | 2/1993 | Domb |
| 5,206,219 A | 4/1993 | Desai |
| 5,213,808 A | 5/1993 | Bar-Shalom |
| 5,227,165 A | 7/1993 | Domb et al. |
| 5,227,298 A | 7/1993 | Weber et al. |
| 5,244,925 A | 9/1993 | Wretlind et al. |
| 5,256,547 A | 10/1993 | Rudat et al. |
| 5,272,068 A | 12/1993 | Ruby et al. |
| 5,300,529 A | 4/1994 | Narayanan |

(Continued)

FOREIGN PATENT DOCUMENTS

CH 679118 A5 9/1989

(Continued)

OTHER PUBLICATIONS

Fujimoto et al. "Effect of Ischemia-Reperfusion on Lipid Digestion and Absorption in Rate Intestine", AJP—Gastrointesinal and Liver Physiology, 260(4): G595-G602, 1991. Abstract.

(Continued)

*Primary Examiner*—Anand U Desai
(74) *Attorney, Agent, or Firm*—D Graeser Ltd (57) ABSTRACT

A novel cyclosporine formulation, which is a pro-nanodispersion at room temperature, featuring solid particles of a relatively large particle size (at least about 150 nm) and yet which is a nanodispersion at body temperature.

13 Claims, 2 Drawing Sheets

U.S. PATENT DOCUMENTS

| | | |
|---|---|---|
| 5,340,588 A | 8/1994 | Domb |
| 5,342,625 A | 8/1994 | Hauer et al. |
| 5,350,741 A | 9/1994 | Takada |
| 5,364,632 A | 11/1994 | Benita et al. |
| 5,376,688 A | 12/1994 | Morton et al. |
| 5,378,475 A | 1/1995 | Smith et al. |
| 5,382,655 A | 1/1995 | Szanya et al. |
| 5,409,816 A | 4/1995 | Lundell et al. |
| 5,430,017 A | 7/1995 | Antalne et al. |
| 5,430,021 A | 7/1995 | Rudnic et al. |
| 5,444,041 A | 8/1995 | Owen et al. |
| 5,447,854 A | 9/1995 | Goto et al. |
| 5,450,512 A | 9/1995 | Asakura |
| 5,468,503 A | 11/1995 | Yamada |
| 5,472,706 A | 12/1995 | Friedman et al. |
| 5,478,860 A | 12/1995 | Wheeler et al. |
| 5,525,634 A | 6/1996 | Sintov |
| 5,529,785 A | 6/1996 | Dietl |
| 5,532,002 A | 7/1996 | Story |
| 5,536,507 A | 7/1996 | Abramowitz |
| 5,543,393 A | 8/1996 | Kim et al. |
| RE35,338 E | 9/1996 | Haynes |
| 5,560,931 A | 10/1996 | Eickhoff et al. |
| 5,569,464 A | 10/1996 | Endo et al. |
| 5,571,536 A | 11/1996 | Eickhoff |
| 5,573,783 A | 11/1996 | Desieno et al. |
| 5,576,016 A | 11/1996 | Amselem et al. |
| 5,583,105 A | 12/1996 | Kovacs et al. |
| 5,589,455 A | 12/1996 | Woo |
| 5,593,691 A | 1/1997 | Eugster et al. |
| 5,599,534 A | 2/1997 | Himmelstein et al. |
| 5,601,844 A | 2/1997 | Kagayama et al. |
| 5,603,951 A | 2/1997 | Woo |
| 5,608,278 A | 3/1997 | Mey et al. |
| 5,613,022 A | 3/1997 | Odhner et al. |
| 5,614,219 A | 3/1997 | Wunderlich et al. |
| 5,614,491 A | 3/1997 | Walch et al. |
| 5,616,330 A | 4/1997 | Kaufman et al. |
| 5,616,595 A | 4/1997 | Chu et al. |
| 5,620,708 A | 4/1997 | Amkraut et al. |
| 5,626,869 A | 5/1997 | Nyqvist et al. |
| 5,633,226 A | 5/1997 | Owen et al. |
| 5,635,491 A | 6/1997 | Seki et al. |
| 5,637,317 A | 6/1997 | Dietl |
| 5,639,474 A | 6/1997 | Woo |
| 5,639,724 A | 6/1997 | Cavanak |
| 5,641,745 A | 6/1997 | Ramtoola |
| 5,645,856 A | 7/1997 | Lacy et al. |
| 5,646,109 A | 7/1997 | Owen et al. |
| 5,648,096 A | 7/1997 | Gander et al. |
| 5,650,170 A | 7/1997 | Wright et al. |
| 5,651,980 A | 7/1997 | Lanza et al. |
| 5,653,987 A | 8/1997 | Modi et al. |
| 5,656,277 A | 8/1997 | Berlati et al. |
| 5,656,287 A | 8/1997 | Adler-Moore et al. |
| 5,656,289 A | 8/1997 | Cho et al. |
| 5,656,459 A | 8/1997 | Balaraman et al. |
| 5,660,856 A | 8/1997 | Adler-Moore et al. |
| 5,660,858 A | 8/1997 | Parikh et al. |
| 5,662,932 A | 9/1997 | Amselem et al. |
| 5,665,379 A | 9/1997 | Hersloef et al. |
| 5,665,386 A | 9/1997 | Benet et al. |
| 5,670,166 A | 9/1997 | Adler-Moore et al. |
| 5,670,478 A | 9/1997 | Stuchlik et al. |
| 5,683,714 A | 11/1997 | Adler-Moore et al. |
| 5,686,105 A | 11/1997 | Kelm et al. |
| 5,686,106 A | 11/1997 | Kelm |
| 5,688,525 A | 11/1997 | Adler-Moore et al. |
| 5,688,528 A | 11/1997 | Carlsson et al. |
| 5,702,727 A | 12/1997 | Amkraut et al. |
| 5,707,648 A | 1/1998 | Yiv |
| 5,709,797 A | 1/1998 | Bocchiola et al. |
| 5,716,928 A | 2/1998 | Benet et al. |
| 5,726,181 A | 3/1998 | Hausheer et al. |
| 5,731,355 A | 3/1998 | Jones et al. |
| 5,739,105 A | 4/1998 | Kim et al. |
| 5,741,512 A | 4/1998 | Hauer et al. |
| 5,741,822 A | 4/1998 | Yesair |
| 5,747,066 A | 5/1998 | Pittrof et al. |
| 5,747,330 A | 5/1998 | Casareto et al. |
| 5,750,142 A | 5/1998 | Friedman et al. |
| 5,756,450 A | 5/1998 | Hahn et al. |
| 5,759,566 A | 6/1998 | Poli et al. |
| 5,759,997 A | 6/1998 | Cavanak |
| 5,766,629 A | 6/1998 | Cho et al. |
| 5,776,488 A | 7/1998 | Mori et al. |
| 5,785,994 A | 7/1998 | Wong et al. |
| 5,788,988 A | 8/1998 | Soon-Shiong et al. |
| 5,798,333 A | 8/1998 | Sherman |
| 5,801,020 A | 9/1998 | Casareto et al. |
| 5,817,320 A | 10/1998 | Stone |
| 5,827,822 A | 10/1998 | Floch et al. |
| 5,830,505 A | 11/1998 | Fischer et al. |
| 5,856,141 A | 1/1999 | Kim et al. |
| 5,858,401 A | 1/1999 | Bhalani et al. |
| 5,858,410 A | 1/1999 | Muller et al. |
| 5,866,159 A | 2/1999 | Hauer et al. |
| 5,874,572 A | 2/1999 | Kim et al. |
| 5,891,845 A | 4/1999 | Myers |
| 5,891,846 A | 4/1999 | Ishida et al. |
| 5,912,005 A | 6/1999 | Lanza et al. |
| 5,916,589 A | 6/1999 | Hauer et al. |
| 5,929,030 A | 7/1999 | Hamied et al. |
| 5,932,243 A | 8/1999 | Fricker et al. |
| 5,948,825 A | 9/1999 | Takahashi et al. |
| 5,958,378 A | 9/1999 | Waldrep et al. |
| 5,958,458 A | 9/1999 | Norling et al. |
| 5,958,876 A | 9/1999 | Woo |
| 5,962,014 A | 10/1999 | Hauer et al. |
| 5,962,017 A | 10/1999 | Hauer et al. |
| 5,962,019 A | 10/1999 | Cho et al. |
| 5,962,522 A | 10/1999 | Wacher et al. |
| 5,965,160 A | 10/1999 | Benita et al. |
| 5,968,972 A | 10/1999 | Broder et al. |
| 5,976,381 A | 11/1999 | Lundell et al. |
| 5,976,436 A | 11/1999 | Livesley et al. |
| 5,977,066 A | 11/1999 | Cavanak |
| 5,980,939 A | 11/1999 | Kim et al. |
| 5,985,248 A | 11/1999 | Gordon et al. |
| 5,985,321 A | 11/1999 | Brox et al. |
| 5,986,072 A | 11/1999 | Handa et al. |
| 5,989,583 A | 11/1999 | Amselem |
| 5,998,365 A | 12/1999 | Sherman |
| 6,001,391 A | 12/1999 | Zeidler et al. |
| 6,004,573 A | 12/1999 | Rathi et al. |
| 6,004,580 A | 12/1999 | Backlund et al. |
| 6,004,583 A | 12/1999 | Plate et al. |
| 6,004,927 A | 12/1999 | Benet et al. |
| 6,007,840 A | 12/1999 | Hauer et al. |
| 6,008,191 A | 12/1999 | Singh et al. |
| 6,008,192 A | 12/1999 | Al-Razzak et al. |
| 6,009,690 A | 1/2000 | Rosenberg et al. |
| 6,010,719 A | 1/2000 | Remon et al. |
| 6,011,011 A | 1/2000 | Hageman |
| 6,013,665 A | 1/2000 | DeMichele et al. |
| 6,020,315 A | 2/2000 | Bosslet et al. |
| 6,022,852 A | 2/2000 | Klokkers et al. |
| 6,024,976 A | 2/2000 | Miranda et al. |
| 6,024,978 A | 2/2000 | Hauer et al. |
| 6,027,747 A | 2/2000 | Terracol et al. |
| 6,028,067 A | 2/2000 | Hong et al. |
| 6,030,941 A | 2/2000 | Summerton et al. |
| 6,045,826 A | 4/2000 | Borowy-Borowski et al. |
| 6,046,163 A | 4/2000 | Stuchlik et al. |

| | | | | | | |
|---|---|---|---|---|---|---|
| 6,048,550 | A | 4/2000 | Chan et al. | EP | 0494716 | 8/1996 |
| 6,051,253 | A | 4/2000 | Zettler et al. | EP | 0659084 | 3/1997 |
| 6,051,257 | A | 4/2000 | Kodas et al. | EP | 0793966 A1 | 3/1997 |
| 6,051,607 | A | 4/2000 | Greff | EP | 0519144 | 8/1997 |
| 6,054,428 | A | 4/2000 | Pierpaoli et al. | EP | 0724452 B1 | 9/1999 |
| 6,057,289 | A | 5/2000 | Mulye | EP | 0710103 | 6/2001 |
| 6,063,762 | A | 5/2000 | Hong et al. | EP | 1174136 | 1/2002 |
| 6,083,521 | A | 7/2000 | Acemoglu et al. | EP | 0910388 | 9/2002 |
| 6,197,335 | B1 | 3/2001 | Sherman | EP | 1018340 | 9/2003 |
| 6,255,100 | B1 | 7/2001 | Ko et al. | EP | 0781125 | 12/2003 |
| 6,267,985 | B1 | 7/2001 | Chen et al. | FR | 2 636 534 A1 | 9/1989 |
| 6,306,306 | B1 | 10/2001 | Voigt et al. | FR | 2636534 A1 | 9/1989 |
| 6,388,789 | B1 | 5/2002 | Bernstein | GB | 1171125 | 11/1969 |
| 6,403,122 | B1 | 6/2002 | Andrysek et al. | GB | 2098865 | 1/1982 |
| 7,026,290 | B1 | 4/2006 | Dumbetal | GB | 2206119 | 12/1988 |
| 2001/0025025 | A1 | 9/2001 | Viskov | GB | 2209671 | 5/1989 |
| 2003/0022944 | A1 | 1/2003 | Gumkowski et al. | GB | 2211848 | 7/1989 |
| | | | | GB | 2222770 | 3/1990 |

FOREIGN PATENT DOCUMENTS

| | | | | | |
|---|---|---|---|---|---|
| | | | GB | 2 278 780 | 5/1994 |
| DE | 3930928 C2 | 9/1989 | IE | 60764 | 9/1989 |
| EP | 0034567 B1 | 2/1981 | JP | 61-249918 | 7/1986 |
| EP | 0135171 | 3/1985 | JP | 61-280435 | 12/1986 |
| EP | 0170623 | 5/1986 | SE | 514303 | 9/1915 |
| EP | 0243446 B1 | 10/1986 | WO | WO 86/01715 | 3/1986 |
| EP | 0124495 | 1/1987 | WO | WO 86/02264 | 4/1986 |
| EP | 0211258 | 2/1987 | WO | WO 87/01035 | 2/1987 |
| EP | 0256856 | 2/1988 | WO | WO 88/00059 | 1/1988 |
| EP | 0287036 B1 | 4/1988 | WO | WO 92/19237 | 11/1992 |
| EP | 0296122 B1 | 6/1988 | WO | WO 93/15736 | 8/1993 |
| EP | 0274431 | 7/1988 | WO | WO 94/15464 | 7/1994 |
| EP | 0418248 B1 | 2/1989 | WO | WO95/01785 | 1/1995 |
| EP | 0174726 | 4/1989 | WO | WO 95/01786 | 1/1995 |
| EP | 0633029 B1 | 4/1989 | WO | WO 95/31110 | 11/1995 |
| EP | 0314689 | 5/1989 | WO | WO96/12031 | 4/1996 |
| EP | 0444081 B1 | 11/1989 | WO | WO96/12032 | 4/1996 |
| EP | 0347843 | 12/1989 | WO | WO96/13273 | 5/1996 |
| EP | 0379708 B1 | 12/1989 | WO | WO 96/14079 | 5/1996 |
| EP | 0379045 B1 | 1/1990 | WO | WO96/27607 | 9/1996 |
| EP | 0388152 B1 | 3/1990 | WO | WO 96/27607 | 9/1996 |
| EP | 0474647 B1 | 3/1990 | WO | WO96/36316 | 11/1996 |
| EP | 0361928 | 4/1990 | WO | WO 96/36316 | 11/1996 |
| EP | 0391369 B1 | 4/1990 | WO | WO97/07787 | 3/1997 |
| EP | 0429248 | 11/1990 | WO | WO 97/07787 | 3/1997 |
| EP | 0502119 B1 | 11/1990 | WO | WO 97/10849 | 3/1997 |
| EP | 0521074 B1 | 3/1991 | WO | WO97/19692 | 6/1997 |
| EP | 0507968 B1 | 4/1991 | WO | WO 97/20548 | 6/1997 |
| EP | 0512109 B1 | 11/1991 | WO | WO97/22358 | 6/1997 |
| EP | 0724429 B1 | 2/1992 | WO | WO97/26003 | 7/1997 |
| EP | 0580817 B1 | 4/1992 | WO | WO97/34918 | 9/1997 |
| EP | 0539319 B1 | 6/1992 | WO | WO97/36610 | 10/1997 |
| EP | 0237200 | 7/1992 | WO | WO 97/39749 | 10/1997 |
| EP | 0244380 | 1/1993 | WO | WO 97/44053 | 11/1997 |
| EP | 0572942 B1 | 5/1993 | WO | WO97/46575 | 12/1997 |
| EP | 0589843 A1 | 9/1993 | WO | WO97/46580 | 12/1997 |
| EP | 0598337 B1 | 11/1993 | WO | WO97/48410 | 12/1997 |
| EP | 0677116 B1 | 12/1993 | WO | WO 98/05309 | 2/1998 |
| EP | 0609001 | 3/1994 | WO | WO 98/07414 | 2/1998 |
| EP | 0635261 B1 | 7/1994 | WO | WO 98/10747 | 3/1998 |
| EP | 0697214 A1 | 7/1994 | WO | WO98/30204 | 7/1998 |
| EP | 0649651 A1 | 9/1994 | WO | WO 98/30205 | 7/1998 |
| EP | 0724452 B1 | 9/1994 | WO | WO98/33512 | 8/1998 |
| EP | 0726760 B1 | 10/1994 | WO | WO98/40051 | 9/1998 |
| EP | 0651995 B1 | 11/1994 | WO | WO98/42734 | 10/1998 |
| EP | 0740547 B1 | 1/1995 | WO | WO 98/58629 | 12/1998 |
| EP | 0725076 A1 | 2/1995 | WO | WO99/00002 | 1/1999 |
| EP | 0756489 B1 | 5/1995 | WO | WO 99/34830 | 7/1999 |
| EP | 0769938 B1 | 6/1995 | WO | WO 99/45946 | 9/1999 |
| EP | 0801686 B1 | 7/1995 | WO | WO99/56727 | 11/1999 |
| EP | 0760237 A1 | 8/1995 | WO | WO00/03753 | 1/2000 |
| EP | 0536343 | 9/1995 | WO | WO00/06120 | 2/2000 |
| EP | 0682879 | 11/1995 | WO | WO/00/18374 | 4/2000 |
| EP | 0799013 B1 | 12/1995 | WO | WO00/18374 | 4/2000 |
| | | | WO | WO00/30615 | 6/2000 |

| WO | WO 00/40219 | 7/2000 |
| WO | WO00/40219 | 7/2000 |
| WO | WO00/72867 | 12/2000 |
| WO | WO 01/12229 | 2/2001 |
| WO | WO2006/001963 | 1/2006 |

OTHER PUBLICATIONS

Muralidhara et al. "Intestinal Absorption of Alpha-Tocopherol in the Unanesthetized Rat. The Influence of Luminal Constituents on the Absorptive Process", Journal of Laboratory and Clinical Medicine, 90: 85-91, 1977. Abstract.

Alvarez et al. "The Role of Calcium Ions and Bile Salts on the Pancreatic Lipase-Catalyzed Hydrolysis of Triglyceride Emulsions Stabilized with Lecitin", Pharmaceutical Research, 6(6): 449-457, 1989.

Bates et al. "Bioavailability of Micronized Griseofulvin From Corn Oil-In-Water Emulsion, Aqueous Suspension, and Commercial Tablet Dosage Forms in Humans", Journal of Pharmaceutical Sciences, 64(5): 793-797, 1975.

Bernkop-Schnürch "The Use of Inhibitory Agents to Overcome the Enzymatic Barrier to Perorally Administered Therapeutic Peptides and Proteins", Journal of Controlled Release, 52: 1-16, 1998. Abstract.

Charman et al. "Physicochemical and Physiological Mechanism for the Effects of Food on Drug Absorption: The Role of Lipids and pH", Journal of Pharmaceutical Sciences, 86(3): 269-282, 1997. Abstract.

Gennaro "Colloidal Dispersions", Remington's Pharmaceutical Sciences, 17th Ed., Chap.20, p. 293-300, 1985.

Hörter et al. "Influence of Physicochemical Properties on Dissolution of Drugs in the Gastrointestinal Tract", Advanced Drug Delivery Reviews, 25:3-14, 1997.

Humberstone et al. "Lipid-Based Vehicles for the Oral Delivery of Poorly Water Soluble Drugs", Advanced Drug Delivery Reviews, 25:103-128, 1997.

Hutchison "Digestible Emulsions and Microemulsions for Optimum Oral Delivery of Hydrophobic Drugs", Journal Technique Gattefossé, 87: 67-74, 1994.

Johnson "Gastrointestinal Physiology", Department of Physiology, University of Texas Medical School, Houston, Texas, p. 25-26, 93, 106, 133-134, 136-137, 1977.

LeCluyse et al. "In Vitro Models for Selection of Development Candidates. Permeability Studies to Define Mechanisms of Absorption Enhancement", Advanced Drug Delivery Reviews, 23: 163-183, 1997.

MacGregor et al. "Influence of Lipolysis on Drug Absorption From the Gastro-Intestinal Tract", Advanced Drug Delivery Reviews, 25: 33-46, 1997.

Pouton "Formulation of Self-Emulsifying Drug Delivery Systems", Advanced Drug Delivery Reviews, 25: 47-58, 1997.

Reymond et al. "In Vitro Model for Ciclosporin Intestinal Absorption in Lipid Vehicles", Pharmaceutical Research, 5(10): 677-679, 1987.

Tarr et al. "Enhanced Intestinal Absorption of Cyclosporine in Rats Through the Reduction of Emulsion Droplet Size", Pharmaceutical Research, 6(1): 40-43, 1989.

Wilson et al. "The Behaviour of Fats and Oils in the Upper G.I. Tract", Bulletin Technique Gattefossé, 90: 13-18, 1997.

Winne "Dependence of Intestinal Absorption In Vivo on the Unstirred Layer", Archives of Pharmacology, 304: 175-181, 1978.

Ekman "[3H]Cholesterol Transfer From Microemulsion Particles of Different Sizes to Human Fibroblasts", Lipids, 22(9): 657-663, 1987. Abstract.

Takada et al. "Enhanced Selective Lymphatic Delivery of Cyclosporin A by Solubilizers and Intensified Immunosuppressive Activity Against Mice Skin Allograft", Pharmaceutical Research, 3(1): 48-51, 1986. Abstract.

Yanagawa et al. "Selective Transfer of Cyclosporin to Thoracic Lymphatic Systems by the Application of Lipid Microspheres", Journal of Microencapsulation, 6(2): 161-164, 1989. Abstract.

Zhi et al. "Effects of Dietary Fat on Drug Absorption", Clinical Pharmacology & Therapeutics, 58(5): 487-491, 1995.

Office action for corresponding European application, Jan. 14, 2009, EP.

IPER for corresponding PCT application, Sep. 12, 2008, WO.

Dara Stevenson et al Efficacy and Safety of Cyclosporin A Ophthalmic Emulsion in the treatment of moderate-to-severe Dry Eye Disease. Ophthalmology 2000:107:967-974.

US 5,543,395, 08/1996, Kim et al. (withdrawn)

Figure 1

Figure 2

PRO-NANODISPERSION FOR THE DELIVERY OF CYCLOSPORIN

RELATED APPLICATIONS

The present application is a Continuation-In-Part (CIP) of U.S. Pat. No. 7,026,290, granted on Apr. 11, 2006 from U.S. patent application Ser. No. 09/869,519, filed on Sep. 17, 2001, which is a U.S. National Phase Patent Application of PCT Patent Application No. PCT/IL99/00710, filed on Dec. 30, 1999, which claims priority from U.S. patent application Ser. No. 09/223,378, filed on Dec. 30, 1998, now abandoned, the contents of which are incorporated herein by reference.

FIELD OF THE INVENTION

The present invention is of a pro-nanodispersion preparation for the delivery of cyclosporin, and in particular, of a pro-nanodispersion preparation which provides a delivery system with high bioavailability of cyclosporin and related substances.

BACKGROUND OF THE INVENTION

Many dispersion systems are currently in use as, or being explored for use as, carriers of substances, particularly biologically active compounds. These systems are designed to protect the substance from the environment during delivery and to provide a controlled release of the substance to a targeted area. In some cases, the goal is to target specific sites in the body using the dispersion. In other cases, the goal is to prepare a drug carrier system that acts as a reservoir at the site of injection.

Dispersion systems used for pharmaceutical and cosmetic formulations can be categorized as either suspensions or emulsions. Suspensions are defined as solid particles ranging in size from a few nanometers up to hundreds of microns, dispersed in an aqueous or nonaqueous medium using suspending agents. Solid particles include microspheres, microcapsules, and nanospheres.

Emulsions can be defined as dispersions of one liquid in another, stabilized by an interfacial film of emulsifiers such as surfactants and lipids. Despite their long history, emulsions are used less often today than many other dosage forms due to the inherent instability. Emulsion formulations include water in oil and oil in water emulsions, multiple water/oil/water emulsions, microemulsions, microdroplets, and liposomes.

A microemulsion is a transparent or substantially transparent emulsion which is formed spontaneously or substantially spontaneously when its components are brought into contact.

Microemulsions are thermodynamically stable and contain dispersed particles or droplets of a size less than about 200 nm. Generally microemulsions feature droplets or particles having a mean diameter of less than about 150 nm. These particles may be spherical, although other structures are feasible, such as liquid crystals with lamellar, hexagonal or isotropic symmetries.

Microemulsions are usually stable over periods in excess of 24 hours.

Microemulsions can also be used as a "microemulsion preconcentrate", which is a composition which spontaneously forms a microemulsion in an aqueous medium, for example in water, upon dilution, or in the gastric juices upon oral application. Dilution of the microemulsion in water can be for example from about 1:1 fold to about 1:10 fold dilution.

As noted above, while emulsion based delivery systems are useful for certain applications, the delivering vesicles are subject to physical rupture because of the delicate nature of the liquid/membrane/liquid structure. Emulsion based delivery systems also have relatively short release times. Further, it is difficult to isolate emulsion based vesicles from the aqueous media used for storage for subsequent reconstitution.

In spite of these difficulties, microemulsions have been the only successful delivery systems for certain types or pharmaceutical compounds, particularly compounds such as members of the cyclosporin class, which are cyclic oligopeptides. The cyclosporin class includes substances having pharmaceutical utility, for example as immunosuppressive agents antiparasitic agents and agents for the reversal of multi-drug resistance, as known and described in the art. Examples of such cyclosporins include, but are not limited to, Cyclosporin A (also known as and referred to herein as "Ciclosporin"), Cyclosporin G, [0-(2-hydroxyethyl)-(D) Ser]2-Ciclosporin and [3'-deshydroxy-3'-ket-MeBmt]'-[Val)]2-Ciclosporin.

The first of the cyclosporins to be isolated was the naturally occurring fungal metabolite Ciclosporin (Cyclosporine). Ciclosporin is the cyclosporin of formula (1):

wherein-MeBmt-represents the N-methyl-(4R)-4-but-2E-en-1-y 1-4-methyl-(L) threonyl residue of formula (II):

in which-x-y-is-CH=CH— (trans). Ciclosporin is well known as an immunosupressive agent. In addition, Ciclosporin is being examined for the treatment of autoimmune and inflammatory diseases.

Since the original discovery of Ciclosporin, a wide variety of naturally occurring cyclosporins have been isolated and identified and many further non-natural cyclosporins have been prepared by total or semi-synthetic means or by the application of modified culture techniques. The class comprised by the cyclosporins now includes, for example, the naturally occurring cyclosporins A through Z c.f. Traber et al. Helv. C'hir. Acta. 60: 1247-1255.1977;

Traber et al. Hel v. Chim. Acto. 65: 1655-1667.1982: Kobel el nul., Europ. J. App. Microbio. and Biotech., 14: 273-240 (1982): and von Wartburg et al., Progress in Allergy, 38: 28-45 (1986)], as well as various non-natural cyclosporin derivatives and artificial or synthetic cyclosporins including: the so-called dihydro-cyclosporins, in which the moiety-x-y-of the-MeBmt-residue in Formula (II) above is saturated to give-x-y-of-CH2-CH2-; derivatized cyclosporins (e.g. in which a further substituent is introduced at the a-carbon atom of the sarcosyl residue at the 3-position of the cyclosporin molecule); cyclosporins in which the MeBmt-residue is present in isomeric form (e.g. in which the configuration across positions 6' and 7' of the-MeBmt-residue is cis rather than trans); and cyclosporins in which variant amino acids are incorporated at specific positions within the peptide sequence. Many of these members of the cyclosporin class exhibit pharmaceutical utility which may be comparable to that of Ciclosporin.

Unfortunately, many difficulties have been encountered in the effective administration of Ciclosporin difficulties which appear to be inherent in the nature of the members of the cyclosporin class. Cyclosporins are characteristically highly hydrophobic and thus require a lipophilic carrier. The selection of a suitable carrier is particularly critical for the administration of cyclosporins, as the bioavailability of these compounds is known in the art to be highly variable, depending upon the properties of the carrier. Furthermore, these compounds are known to have bioavailability which may vary significantly between individuals. Such variation is particularly dangerous given the side effects of cyclosporins, such as nephrotoxicity. Thus, the suitable carrier must provide good bioavailability of cyclosporins which is substantially consistent between individuals.

Absorption and metabolism of Cyclosporin are highly variable from patient to patient. Following oral administration the elimination of Cyclosporin is primarily biliary with only 6% of the dose (parent drug and metabolites) excreted in urine. The disposition of the orally administered drug from blood is generally biphasic with a terminal half life in the range of 5-18 hours. The cyclosporine relationship between the administered dose and exposure is linear within the therapeutic dose range.

Following oral administration the Tmax ranges from 1.5-2.0 hours and administration of food is known to shows a slight decrease in AUC and Cmax.

The drug is extensively metabolized by cytochrome P450-3A present in the liver and to a lesser degree by the CYP-3A in the gut and kidney. The drug is also a substrate for the P-glycoprotein (PGP). At least 25 metabolites have been identified in human bile, faeces, blood and urine. The immunosuppressive activity is primarily due to the parent drug (Physician Desk Reference 59$^{th}$ edition, Thomson N J, 2005; 2346-2353).

As noted previously, cyclosporins may be administered with a microemulsion carrier.

According to formulations of such carriers that are known in the art, the carrier generally contains a hydrophilic solvent, such as liquid PEG200-600 ethylene or propylene glycol, ethanol or propanol, Glycerin, water soluble fatty acid C6-C18 esters of sucrose, dimethylisosorbide, ethyl-acetate, glycofurol (fatty acid derivative of a cyclic polyol), PEG derivatives of tocopherol, or PEG-fatty acid esters; a surfactant such as Tween 20, various PEG (polyethylene glycol) derivatives or phospholipids; a water insoluble oil such as corn oil and other oils from plants and mixtures of oils: and Cremophor (polyethoxylated castor oil) and similar PEG derivatives of castor oil or other fats which are used as an amphiphilic solvent, emulsifier, surfactant and so forth. Unfortunately, none of these background art formulations provides high bioavailability for cyclosporin.

The currently commercially available formulation is disclosed in U.S. Pat. No. 5,342,625 to Sandoz A. G. This formulation includes a hydrophilic phase, a lipophilic phase and a surfactant. The hydrophilic phase could be a C 1-5 alkyl di- or partial-ether of a mono- or poly-oxy-C2 2alkanediol, for example.

PCT Application No. WO 96/13273 to Sandoz describes compositions for cyclosporin and other macrolide drugs such as Rapamycin, containing a hydrophilic phase which includes dimethylisosorbide and/or a lower alkyl alkanoic ester, a lipophilic phase and a surfactant. The particle size after dispersion can be 200 nm but is preferably 100 nm or less. The hydrophilic phase is PEG, propylene glycol and glycofurol or dimethylisosorbide (a bicyclic ether). The bioavailability of a composition containing cyclosporin and the carrier is not disclosed.

PCT Application No. WO 97/19692, also to Sandoz, describes compositions which are based on PEG-derivatives of saturated hydroxy fatty acids such as PEG-hydroxystearate and a low alcohol such as ethanol or propylene glycol. Again, the bioavailability of such a composition is not disclosed. PCT Application No. WO 98/33512 to Novartis describes compositions for oral administration of cyclosporin which do not contain oil. Instead, these compositions contain a surfactant with HLB 10 or higher and a hydrophilic phase which is polyethylene glycol and/or a lower alcohol (not more than 12%). The formulations are preconcentrates which provide a particle size of 10 to 150 nm upon dispersion. The disclosed advantage of these compositions is their ability to be stably contained within a hard capsule. However, no specific data is disclosed related to the bioavailability of cyclosporin with this composition. As noted above, the bioavailability of cyclosporin is known to be highly variable, depending upon the carrier.

PCT Application No. WO 97/04795 to POLI Industria describes compositions that must contain one polymer, linear or crosslinked PEG and poly(acrylic) or mixtures thereof and monoesters of fatty acids with a short alcohol. Again, the bioavailability of such a composition is not disclosed.

U.S. Pat. No. to Novartis describes solid formulations for cyclosporin composed of a water soluble monoester of a fatty acid C6-C18 with a polyol, for example a saccharide such as Saccharose monolaurate or raffinose monolaurate. This solvent can be used in combination with other water soluble solvents including PEG, ethanol, ethylene glycol and glycerin. The examples describe solid solutions (powder) of Cyclosporin in saccharose monooleate which is completely soluble in water. Again, the bioavailability of such a composition is not disclosed.

U.S. Pat. Nos. 5,603,951 and 5,639,474 to Hanmi Pham. describe compositions of dimethylisosorbide as a cosurfactant and a primary alcohol, medium chain triglycerides and a surfactant having a HLB value of 10 to 17 such as Tween 20, formulated in soft gelatin capsule.

The particle size is about 100 nm. Again, the bioavailability of such a composition is not disclosed.

U.S. Pat. No. 5,583,105 to Biogel describes cyclosporin formulations composed of PEG esters of tocopherol and a lipophilic solvent, an amphiphilic solvent and ethanol. Again, the bioavailability of such a composition is not disclosed.

U.S. Pat. No. 5,614,491 to Dr. Rentschler GmbH, describes formulations of PEG fatty acid monoesters as emulsifying agent and a polyol as solvent. U.S. Pat. No. 5,798,333 to Sherman describes formulations composed of Tocophersolan and a polyhydric alcohol.

Tocophersolan is a water soluble surfactant which dissolves cyclosporin only at a 7:1 ratio. U.S. Pat. No. 5,827,822 to Sangstat describes formulations of alcohol and a PEG surfactant forming particle size between 200 and 400 nm.

European Patent Application No. EP 0760237 A1 to Cipla describes a composition containing: vegetable oil triglycerides (castor, peanut, or coconut oil), phospholipid, a surfactant (Tween 20, polyoxyl-40-hydrogenated castor oil) and a hydrophilic solvent, propylene glycol.

Again, the bioavailability of cyclosporin administered with such a composition is not disclosed.

None of these disclosed background art carrier formulations features an organic solvent which is a lower alkyl ester of hydroxyalkanoic acid, such as ethyl lactate. Moreover, none of these disclosed background art carrier formulations features a combination of a surfactant with high HLB and a surfactant with low HLB. Furthermore, none of these background art carrier formulations is disclosed as having high bioavailability. Furthermore, none of these background art carrier formulations is disclosed as having a solid fat as a core component which results in a dispersion when mixed with aqueous media at room temperature. Thus, the background art carrier formulations do not appear to possess the advantageous high bioavailability of the present invention, as described in greater detail below.

There is thus an unmet need for, and it would be useful to have, a composition for the administration of cyclosporins, particularly for oral administration, which would provide a high bioavailability, and which would preferably contain an organic solvent which is a lower alkyl ester of hydroxyalkanoic acid and a surfactant which is preferably a combination of a surfactant with high HLB and a surfactant with low HLB.

SUMMARY OF THE INVENTION

The present invention is of a novel formulation for the administration of a cyclosporin.

Unexpectedly, the inventor has found that the novel formulation, which is a pro-nanodispersion at room temperature, featuring solid particles of a relatively large particle size as described in greater detail below, can become a nanodispersion at body temperature. Furthermore, the inventor has discovered that surprisingly the formulation, when stored in soft gelatin capsules at room temperature, is stable for more than 2 years, maintaining the same composition and particle size. Furthermore, the novel formulation provides excellent bioavailability characteristics as described in greater detail below.

The formulation according to the present invention features an amphiphilic solvent which is characterized by being a lower alkyl ester of hydroxyalkanoic acid; a surfactant, preferably a combination of a surfactant with a high HLB (hydrophilic/lipophilic balance) and a surfactant with a low HLB; and optionally and preferably comprising a solid fat. The solid fat is a fat which is solid at room temperature but which preferably melts at a temperature of at least about 30 C and which more preferably melts at body temperature, such as a fatty acid ester. Preferably, the solid fat comprises a triglyceride such as tricaprin. Other non-limiting examples of suitable solid fats include trilaurin, fatty acids and fatty alcohols of 10 carbons or more, esters of fatty acids such as ethyl stearate and hydrogenated triglycerides that are solid at room temperature and melt at a temperature of at least about 30 C, more preferably melting at body temperature.

Optionally and more preferably, there is a large difference between the HLB of the low HLB surfactant and that of the high HLB surfactant, such that the low HLB surfactant preferably has an HLB of less than about 6, while the high HLB surfactant preferably has an HLB of greater than about 10. More preferably, the low HLB surfactant has an HLB of less than about 4, while the high HLB surfactant has an HLB of greater than about 14. The high HLB surfactant preferably comprises Polysorbate 20 (for example Tween 20) and the low HLB surfactant preferably comprises Sorbitan oleate (for example Span 80). Polysorbate 20 has an HLB of 16.7, while Sorbitan oleate has an HLB of 4.3.

The formulation also preferably features a phospholipid and an ethoxylated fat such as Cremophor or Poloxamers which are block copolymers of polyethylene glycol and polypropylene glycol.

According to preferred embodiments of the present invention, there is provided a composition for administering a cyclosporin compound, the composition comprising: (a) a pro-nanodispersion characterized by being capable of forming, upon contact with an aqueous solution, particles of a size of less than about 100 nm at a temperature of at least about 30° C., the pro-nanodispersion comprising: (i) at least one surfactant; and (ii) an amphiphilic solvent comprising a lower alkyl hydroxyalkanoic acid ester; and (b) a pharmaceutically effective amount of the cyclosporin compound.

Preferably, the lower alkyl hydroxy alkanoic acid ester comprises ethyl lactate. Preferably, the at least one surfactant is a combination of at least two surfactants, at least one surfactant of the combination being a hydrophilic surfactant, and at least one surfactant of the combination being a hydrophobic surfactant. Preferably, the hydrophilic surfactant has an HLB (hydrophilic/lipophilic balance) of at least about 10. More preferably, the hydrophilic surfactant has an HLB of at least about 14. More preferably, the hydrophobic surfactant has an HLB of less than about 5. Most preferably, the hydrophobic surfactant comprises a sorbitan fatty acid ester.

Optionally and preferably, the combination is a combination of polyoxyethylene (20) sorbitan monolaurate and sorbitan monooleate.

According to preferred embodiments, the composition further comprises an ethoxylated fat. More preferably, the ethoxylated fat is selected from the group consisting of polyethyleneglycol-hydrogenated castor oils. Most preferably, the ethoxylated fat is selected from the group consisting of Cremophor and Cremophor RH.

According to preferred embodiments, the composition further comprises a phospholipid. More preferably, the phospholipid comprises lecithin. Most preferably, the phospholipid is selected from the group consisting of egg phospholipid, bovine heart phospholipid and soy phospholipid.

According to preferred embodiments, the composition further comprises a fatty acid ester. More preferably, the fatty acid ester is a solid fat at room temperature. Most preferably, the fatty acid ester comprises triglyceride.

Preferably, the particle size is less than about 60 nm at a temperature of at least about 30° C. More preferably, the particle size is in a range of from about 5 nm to about 50 nm at a temperature of at least about 30° C.

More preferably, the cyclosporin compound is Ciclosporin.

According to preferred embodiments, there is provided a composition for administering a cyclosporin compound, the composition comprising a pharmaceutically effective amount of the above composition, and an aqueous solution as a diluent for the pharmaceutically effective amount of the composition.

According to preferred embodiments, the composition for administering a cyclosporin compound, the composition comprising a lyophilized composition, the lyophilized composition being formed from a pharmaceutically effective amount of the composition and an aqueous solution as a diluent for the pharmaceutically effective amount of the composition to form a diluted solution, the diluted solution being lyophilized to form the lyophilized composition.

According to preferred embodiments, the method for administering a cyclosporin compound to a subject in need of treatment thereof, the method comprising: administering a pharmaceutically effective amount of the composition to the subject. Preferably, the subject is in need of treatment of a condition selected from the group consisting of autoimmune disease and inflammatory conditions. More preferably, the subject is in need of treatment of organ or tissue transplant rejection.

Optionally and preferably, the pharmaceutically effective amount of the composition is administered to the subject through oral administration. More preferably, the pharmaceutically effective amount of the composition is administered as a dispersion with an aqueous solution as a diluent.

Preferably, the pharmaceutically effective amount of the composition is administered to the subject through topical administration. More preferably, the pharmaceutically effective amount of the composition is administered to the subject through parenteral administration.

Preferably, the pharmaceutically effective amount of the composition is administered as a capsule. More preferably, the pharmaceutically effective amount of the composition is administered as a tablet. Most preferably, the pharmaceutically effective amount of the composition is administered as a powder.

According to preferred embodiments, the method for determining storage stability of a formulation containing a cyclosporin compound, the method comprising the step of analyzing the composition for particle size, such that if the particle size is less than about 100 nm, the formulation is determined to be stable.

According to preferred embodiments, the composition for administering a cyclosporin compound, the composition comprising: (a) a pro-nanodispersion characterized by being capable of forming, upon contact with an aqueous solution particles of a size of less than about 100 nm at a temperature of at least about 30° C., the pro-nanodispersion comprising: (i) an ethoxylated fat; and (ii) an amphiphilic solvent comprising a lower alkyl hydroxyalkanoic ester or a lower alkyl ester of N-alkyl pyrrolidone; and (b) a pharmaceutically effective amount of the cyclosporin compound. Preferably, the ethoxylated fat is selected from the group consisting of polyethyleneglycol-hydrogenated castor oils. More preferably, the ethoxylated fat is selected from the group consisting of Cremophor and Cremophor RH 60.

Preferably, the amphiphilic solvent includes a lower alkyl hydroxy alkanoic acid ester. More preferably, the amphiphilic solvent includes ethyl lactate.

According to preferred embodiments, there is provided a method for administering a cyclosporin compound to a subject in need thereof, the method comprising: administering a pharmaceutically effective amount of a composition, the composition comprising a pro-nanodispersion characterized by being capable of forming, upon contact with an aqueous solution, particles of a size of less than about 100 mm at a temperature of at least about 30° C., the pro-nanodispersion comprising at least one surfactant and an amphiphilic solvent comprising ethyl lactate.

According to preferred embodiments, there is provided a composition for administering a cyclosporin compound, the composition comprising: (a) a pro-nanodispersion characterized by being capable of forming at room temperature, upon contact with an aqueous solution, a solid particulate suspension containing the cyclosporin compound, and being capable of forming particles of a size of less than about 100 nm at a temperature of at least about 30° C., the pro-nanodispersion comprising (i) at least one surfactant; and (ii) an amphiphilic solvent comprising a lower alkyl hydroxy alkanoic acid ester; and (b) a pharmaceutically effective amount of the cyclosporin compound.

According to preferred embodiments, the composition for administering a cyclosporin compound, the composition comprising: (a) a pro-nanodispersion characterized by being capable of forming, upon contact with an aqueous solution, a solid particulate suspension containing the cyclosporin compound, the pro-nanodispersion comprising: (i) a solid fat; and (ii) an amphiphilic solvent comprising a lower alkyl hydroxy alkanoic acid ester; and (b) a pharmaceutically effective amount of the cyclosporin compound.

Preferably, the particulate suspension contains particles of a size of at least about 100 nm at room temperature.

According to preferred embodiments, there is provided a composition for administering a cyclosporin compound, the composition comprising: (a) a pro-nanodispersion characterized by being capable of forming, upon contact with an aqueous solution, a solid particulate suspension containing the cyclosporin compound, the pro-nanodispersion comprising: (i) a solid fat; an (ii) ethyl lactate; and (b) a pharmaceutically effective amount of the cyclosporin compound.

Preferably, the pro-nanodispersion further comprises a low HLB surfactant and a high HLB surfactant. More preferably, a difference between the HLB values for the low and the high HLB surfactants is at least about 5 units. Most preferably, the low HLB surfactant comprises polysorbate 20 and wherein the high HLB surfactant comprises sorbitan monooleate.

Preferably, the solid fat comprises Tricaprin. According to preferred embodiments, the formulation further comprises an ethoxylated fat.

According to preferred embodiments, there is provided a novel cyclosporine formulation comprising ethyl lactate and a solid fat as carrier, and cyclosporine as active ingredient, characterized in that the formulation is a pro-nanodispersion at room temperature, featuring solid particles of at least about 150 nm, but is a nanodispersion at body temperature, featuring solid particles of less than about 100 nm.

According to preferred embodiments, there is provided a composition for administering a cyclosporin compound, the composition comprising: (a) a pro-nanodispersion comprising: (i) a solid fat; (ii) ethyl lactate; (iii) at least two surfactants comprising a low HLB surfactant and a high HLB surfactant, wherein a difference between the HLB values for the low and the high HLB surfactants is at least about 5 units; and (iv) an ethoxylated fat; and (b) a pharmaceutically effective amount of the cyclosporin compound.

According to preferred embodiments, the formulation further comprises a suitable diluent for administration to the eye.

According to preferred embodiments, there is provided a formulation for topical administration to the eye, comprising: (a) a pro-nanodispersion comprising (i) a solid fat; (ii) an amphiphilic solvent; (iii) at least one hydrophilic surfactant; and (b) a pharmaceutically effective amount of the cyclosporin compound; wherein the components are adapted for administration to the eye.

Preferably, the cyclosporine is present in an amount of from about 0.01 to about 1.0% (w/v).

More preferably, the cyclosporine is present in an amount of about 0.1% (w/v).

Preferably, the hydrophilic surfactant comprises Polysorbate 20. More preferably, the polysorbate 20 comprises from about 0.3 to about 4 mg per ml of the final formulation.

Preferably, the formulation further comprises a low HLB surfactant, wherein a difference between the HLB values for the low HLB surfactant and the hydrophilic surfactant is at least about 5 units. More preferably, the low HLB surfactant comprises sorbitan oleate. Most preferably, the sorbitan oleate is present in an amount of from about 0.3 to about 4 mg per ml of the final formulation.

Preferably, the solid fat comprises tricaprin or ethyl stearate, or a combination thereof. More preferably, the solid fat comprises tricaprin. Most preferably, the tricaprin is present in an amount of from about 0.3 to about 3 mg per ml of the final formulation. Preferably, the surfactant further comprises an ethoxylated fat. More preferably, the ethyoxylated fat comprises macrogolglycerol hydroxystearate. Most preferably, the macrogolglycerol hydroxystearate is present in an amount of from about 0.1 to about 2 mg per ml of the final formulation.

Preferably, the solvent comprises ethyl lactate. More preferably, the solvent comprises N-methylpyrrolidone.

Preferably, the formulation further comprises a phospholipid. Preferably, the phospholipid comprises lecithin. Most preferably, the lecithin is present in an amount of from about 0.1 to about 2 mg per ml of the final formulation.

According to preferred embodiments, the formulation preferably further comprises a suitable diluent. According to preferred embodiments, there is provided a method of a treatment of a condition of the eye, comprising administering the formulation above to the eye.

Preferably, the formulation further comprises a suitable diluent and wherein the suitable diluent is stored separately from the formulation comprising the active ingredient and wherein prior to the administering the formulation, the suitable diluent is mixed with the formulation.

The preferred mean diameter of the particle of the resultant formulation is preferably greater than about 150 nm at room temperature (25 C) upon contact with water but is preferably less than about 100 nm, more preferably less than about 60 nm, and most preferably from about 5 nm to about 50 nm from at least about 33 C, such that this particle size is achieved at body temperature. Hereinafter, the term "pro-nanodispersion" includes those compositions featuring droplets or particles having a mean diameter of greater than about 150 nm at room temperature, and which forms a nanodispersion in an aqueous medium, for example in water upon dilution from at least about 30 C, or in the gastric juices after oral intake. Dilution of the Pro-nanodispersion in water can be for example from about 1:1 fold to about 1:1000 fold dilution. Hereinafter, the term "nano-dispersion" refers to a dispersion in an aqueous medium of particles or vesicles of 100 nanometers or less at body temperature.

BRIEF DESCRIPTION OF THE DRAWINGS

The invention is herein described, by way of example only, with reference to the accompanying drawings, wherein:

FIG. 1 shows the mean percent of drug (CsA) released versus time for test (Dexcel Ltd) (□) and reference Neoral®100 mg from Novartis (■) using USP 24 method. Both test and reference products exhibited very similar dissolution profiles; and FIG. 2 shows the mean CsA concentration-time profiles alter single oral administration of 200 mg of the drug given as soft gelatin capsules test (□) (Dexcel Ltd.) and known drug reference Neoral® 200 ma (Novartis Inc.) (■) to 24 healthy volunteers.

DESCRIPTION OF THE PREFERRED EMBODIMENTS

The present invention is of a novel formulation for the administration of a cyclosporin.

This formulation features an amphiphilic solvent which is characterized by being a lower alkyl ester of hydroxyalkanoic acid; and a surfactant, preferably a combination of a surfactant with a high HLB (hydrophilic/lipophilic balance) and a surfactant with a low HLB. Optionally and preferably, the formulation further features a solid fat that is solid at room temperature but preferably melts at a temperature above 30° C. The high HLB surfactant preferably comprises Polysorbate 20 (for example Tween 20) and the low HLB surfactant preferably comprises Sorbitan oleate (for example Span 80). The amphiphilic solvent is preferably ethyl lactate. Ethyl lactate is an amphiphilic solvent characterized by having an octanol/water coefficient of 0.06. The solid fat is preferably a fatty acid ester and is more preferably a triglyceride.

The formulation optionally and preferably comprises a phospholipid. Optionally and more preferably, the formulation comprises an ethoxylated fat such as Cremophor or another similar substance.

Hereinafter, the terms "solid fat" and "liquid fat" refer to fats which are solid or liquid, respectively, at room temperature. Preferably, the composition of the present invention does not include an alkyl alcohol such as ethanol.

Preferably the ethoxylated fat is selected from the group consisting of polyethyleneglycol-hydrogenated castor oils. More preferably, the ethoxylated fat is selected from the group consisting of polyoxyl castor oil (preferably Cremophor) and polyoxyl hydrogenated castor oil (preferably Cremophor RH).

The preferred particle size of the resultant formulation from at least about 30° C. is less than about 100 nm, more preferably less than about 60 nm, and most preferably from about 5 nm to about 50 nm. In fact, as described in greater detail below, the resultant formulation must have a particle size of less than about 100 nm at body temperature in order to be suitable for the administration of cyclosporin. Surprisingly, it was discovered that the particle size at room temperature of the formulation of the present invention is at least about 150 nm, as the formulation forms a solid nanodispersion, yet contrary to the teachings of the art, is still able to achieve a suitable particle size upon administration to a subject.

Furthermore, surprisingly the inventor has discovered that the particle size at room temperature does not control bioavailability, which is contrary to the teachings of the background art. It is possible to have formulations with the taught particle size at room temperature that exhibit poor bioavailability, while other formulations (such as the formulation of the present invention) may have particle sizes greater than that taught by the background art, yet may still have excellent bioavailability. Also in direct contradiction to the teachings of the background art, the pro-nanodispersion does not spontaneously form a nanodispersion upon dilution in water of the desired particle size without the application of heat (namely the presence in the body of the subject to obtain particle size of less than 100 nanometers, as body temperature is about 37° C.).

As described in greater detail below, the combination of these components has unexpectedly been shown to provide higher bioavailability than had been previously shown for formulations of cyclosporin. Furthermore, the formulations of the present invention have the advantage of not requiring stabilizers, such as anti-oxidants in order to obtain good stability characteristics. Without wishing to be limited to a single mechanism, it is hypothesized that the excellent stability of the formulations of the present invention is due to the use of solvents such as ethyl lactate as described in greater detail below.

Ethyl lactate, and other members of this family of solvents, have unexpectedly good properties for such a formulation as the formulations of the present invention. For example, ethyl lactate is miscible in both organic and aqueous solvents, since it is more hydrophobic than ethanol. Ethyl lactate has higher storage stability than ethanol. Ethanol is a highly volatile solvent, with correspondingly lower storage stability, such that the use of ethanol in the currently available background art formulations is a clear disadvantage of these formulations.

Furthermore, these background art formulations require a combination of ethanol and propylene glycol in order to stabilize the alcohol, which is another disadvantage of incorporating ethanol into a formulation, a disadvantage which is overcome by the formulations of the present invention.

The present invention may be more readily understood with reference to the following illustrative examples. It should be noted that reference is made generally to "cyclosporin", indicating any member of the cyclosporin class having pharmaceutical efficacy. The particularly preferred member of the cyclosporin class is Ciclosporin (Cyclosporin A). The preparation of the pro-nanodispersion compositions of the present invention is described first with reference to the following general description and then with reference to the following non-limiting examples of the preparation and application of the compositions of the present invention.

Amphiphilic Solvent

First, as noted previously, a suitable organic solvent must be selected. The solvent is preferably selected from the family of lower alkyl esters of hydroxyalkanoic acid. Hereinafter, the term "lower alkyl" includes C1 to C4, for example ethyl. The preferred amphiphilic solvents of the present invention are C1-4 alkyl-hydroxy alkanoic acid ester. More preferably, the amphiphilic solvent comprises ethyl lactate.

Ethyl lactate (2-hydroxypropanoic acid ethyl ester), is a colorless liquid which is miscible with water, alcohol and ether. Ethyl lactate is considered to be suitable for human administration with an LD50 which was higher than 5 g/kg in mice when given an oral dose; however, surprisingly ethyl lactate was not previously taught as a suitable ingredient for pharmaceutical compositions.

Ethyl lactate is amphiphilic and therefore possesses a number of characteristics. For example, the diffusion of ethyl lactate from an organic solution into water is much slower and controlled compared to highly hydrophilic solvents such as ethanol or propanol. This is an important feature as a fast diffusion may result in immediate precipitation when exposed to aqueous media and in the other hand, a too slow diffusing solvent may not form the desired particle size as the formed droplets are not spontaneously formed.

Without wishing to be limited by a single hypothesis, one important parameter for the behavior of the formulation of the present invention is the rate of diffusion of the solvent from the hydrophobic mixture of the pro-nanodispersion, as the rate of diffusion determines the particle size and composition of the formed particles. Again without wishing to be limited by a single hypothesis, a rapid rate of diffusion will result in precipitation of large particles from the aqueous medium, while a slow rate of diffusion from the pro-nanodispersion into the stomach liquid may result in improper particle formation and precipitation of large particles, or alternatively may cause the cyclosporin to be poorly integrated within the solid fat carrier of the present formulation. Also, it may cause one or more components in the stomach fluid to interfere in the process of particle formation. Thus the rate of diffusion from the oil droplet into the aqueous medium is a very important feature, as it must be neither too rapid nor too slow. The diffusion rate is related to the partition coefficient.

The partition coefficient of ethyl lactate is exactly on the border between hydrophobicity and hydrophilicity, with a value of 0.06, which means that 50% of the solvent is in the octanol hydrophobic phase and 50% is in the water phase. Therefore, the diffusion rate is neither slow nor rapid, but in fact is exactly in the middle.

From the chemical view point, ethyl lactate combines the properties of an alcohol and an ester where the ester group provides hydrophobicity while the hydroxyl provides the hydrophilicity and the ability to form hydrogen bonding with water.

Surfactant

Second, a suitable surfactant is preferably selected, which is preferably a combination of a surfactant with a high HLB (hydrophilic/lipophilic balance) of at least about 10 and a surfactant with a low HLB of less than about 6. The term "HLB" refers to the hydrophilic/lipophilic balance of a surfactant. A surfactant with high HLB is hydrophilic, while a surfactant with low HLB is hydrophobic.

Therefore, the combination of a surfactant with high HLB and a surfactant with low HLB, as is preferred for the compositions of the present invention, is actually a combination of a hydrophilic surfactant and a hydrophobic surfactant. This combination has never been taught or suggested in the background art as being suitable for a pharmaceutical carrier for cyclosporins. Where the HLB of the surfactant has been specified in the background art, it has been given in the range of 8 to 20, which is clearly different from the combination of surfactants taught herein. Thus, the compositions of the present invention can be clearly differentiated from those taught in the background art on the basis of the preferred combination of a surfactant with a low HLB and a surfactant with a high HLB.

Particularly preferred combinations of these surfactants feature a large difference between the HLB of the low HLB surfactant and that of the high HLB surfactant. The high HLB surfactant preferably comprises Polysorbate 20 (for example Tween 20) and the low HLB surfactant preferably comprises Sorbitan oleate (for example Span 80). Of course other such combinations could be also be used.

Span hydrophobic surfactants are a group of sorbitan fatty acid esters such as sorbitan monooleate, sorbitan monopalmitate, sorbitan monostearate, sorbitan tristearate, sorbitan monooleate, sorbitan trioleate and sorbitan monolaurate (Fiedler, H. P., "Lexikon der Hilfsstoffe fur Pharmazie, Kosmetic und Angrenzende Gebiete", Editio Cantor, D-7960 Aulendorf, 3rd edition, 1989, pages 1139-1140). Span 80 is an example of a low HLB surfactant, with an HLB of 4.3, and is sorbitan monooleate. They are commercially available from various producers, which include but are not limited to, Capital City Products, Croda Chem, ICI, Lippo Chem. and Atlas, under various commercial names: Arlacel™, Armotan, Crill, Emsorb, Liposorb, Protachem, and Sorbester™. Examples of suitable surfactants from this group with HLB values given in parentheses are as follows: Span 60 (4.7), Span 65 (2.1). Span 80 (4.3), Span 85 (1.8), Arlacel 83 (3.7), Arlacel 85 (1.8), Arlacel 80 (4.3), and Arlacel 60 (4.7). These molecules are generally soluble in oil. They are also soluble in most organic solvents. In water they are generally insoluble but dispersible. Other low HLB surfactants include but are not limited to PEG-6 glyceryl monooleate (HLB of about 3 or 4), and propylene glycol laurate (HLB of 4).

Tween hydrophilic surfactants (Polysorbates) are a family of PEG sorbitan esters (polyoxyethylene-sorbitan-fatty acid esters), for example mono- and tri-lauryl, palmityl, stearyl and oleyl esters of the type known and commercially available under the trade name Tween (Fiedler, H. P., "Lexikon der Hilfsstoffe fur Pharmazie, Kosmetic und Angrenzende Gebiete", Editio Cantor. D-7960 Aulendorf. 3rd edition, 1989, pages 1300-1304). Tween 20 (polyoxyethylene (20) sorbitan monolaurate) has an HLB of 16.7. Other types of Tween surfactants may also be useful for the compositions of the present invention.

Tween surfactants are soluble in water but not in oil. The chemical structure of this family of surfactants features one, two or three short PEG chains, generally of about 5 to 20 ethylene glycol units, connected by an ester bond to sorbitan. These surfactants are produced by various companies (Croda, ICI, Sandoz, Mazer, Atlas) and may appear under various trade names, besides Tween: SorlateT"", Monitan™, CrilletT" and so forth. Members of this family which are polysorbates 20, 21, 0, 60, 61, 65, 80 and 85 have an HLB between 11 and 16.7, and therefore would be suitable for the present invention as high HLB surfactants.

Other suitable high HLB surfactants may be obtained from manufacturers such as Gattefosse Ltd., and include but are not limited to, sucrose fatty acid esters such as saccharose monopalmitate (HLB of 15) and saccharose monostearate (HLB of 11) or PEG-32 glyceryl laurate (HLB of 14). Suitable high HLB nonionic surfactants are polyethylene glycol (PEG) nalkanol esters of the Brij family such as Brij and 99 which have an HLB in the range of 12.4 to 16.9. Brij 56 is polyoxyethylene [10] cetyl ether and is an example of such a high HLB surfactant which can be substituted for Tween 20. Brij 56 has an HLB of 12.9.

Phospholipid

According to preferred embodiments of the present invention, the formulation further comprises a phospholipid. A phospholipid is a phosphorylated diacylglyceride molecule or its derivative. The parent structure is diacylglycerol phosphate, or phosphatidic acid. Phosphatidyl choline (lecithin) is the choline ester of phosphorylated diacylglyceride. Synthetic lecithins are available with acyl chain lengths ranging from 4 to 19 carbons. The preferred lecithins for biological applications are those with alkyl chain lengths in the biological range (10 to 18 carbons). Naturally occurring lecithin can be obtained from a variety of sources such as egg, bovine heart, or soy bean. Unsaturated lecithins (dioleoyl; dilinoleoyl; alpha-palmitoyl, beta oleoyl; alpha palmitoyl, beta linoleoyl; and alpha oleoyl, beta palmitoyl), dianachidonyl lecithin (highly unsaturated and a prostaglandin precursor), and alpha palmito beta myristoyl lecithin are also available.

Certain phospholipids, such as phosphatidic acid, phosphatidyl serine, phosphatidyl inositol, cardiolipin (diphosphatidyl glycerol), and phosphatidyl glycerol, can react with calcium in serum, causing aggregation or the binding of liposheres to cell membranes.

These unfavorable reactions can be minimized by combining these phospholipids with noncalcium binding phospholipids such as phosphatidylcholine. Phosphatidic acid can be isolated from egg or prepared synthetically (dimyristoyl, dipalmitoyl and distearoyl derivatives are available from Calbiochem). Bovine phosphatidyl serine is also available commercially (Sigma Chemical Co. St. Louis, Mo.). Phosphatidyl inositol can be isolated from plant or bovine sources. Cardiolipin can be purified from bovine or bacterial sources. Phosphatidyl glycerol can also be purified from bacterial fermentation.

Solid Fat

Yet another optional ingredient is a solid fat, preferably a fatty acid ester such as a triglyceride. A non-limiting example of such a triglyceride is tricaprin. Tricaprin is a hydrophobic triester of glycerol and caproic acid. Tricaprin does not dissolve in water and thus remains as a component of the dispersed cyclosporin-loaded particles after dispersion in aqueous solution. Tricaprin solubilizes cyclosporin in a fatty medium which is dispersed by the hydrophilic-hydrophobic dispersing agents. Other such fatty components which are suitable as replacement for tricaprin include, but are not limited to, pure and mixed alkyl esters of fatty acids and mixtures thereof. Examples include but are not limited to ethyl esters of fatty acids such as ethylstearate and ethylpalmitate triglycerides such as trilaurin and mixtures of solid fatty acid esters. Mixtures of fats include hydrogenated vegetable oils. The preferred fats are those that solubilize cyclosporin with a melting point between 25 and 37 C such that the resultant pro-nanodispersion formulation forms a nanodispersion of solid particles which melt into a nano-dispersion at body temperature.

The following specific examples illustrate various aspects of the present invention, and are not intending to be limiting in any way. For all experiments described below, unless otherwise stated, the particle size of the pro-nanodispersion was measured with an N4-Coulter particle size analyzer, suitable for submicron particle size determination. Three drops of the pro-nanodispersion were added to five milliliters of water. The particle size of the pro-nanodispersion did not change when the pro-nanodispersion was dispersed in five milliliters of HCl solution. The member of the cyclosporin class which was used for the experiments described below was Ciclosporin (Cyclosporin A).

Example 1

Preferred Formulation

This Example describes a preferred but illustrative formulation according to the present invention. Preferably, the formulation features Ciclosporin as the active ingredient (this Example includes 100 mg of the active ingredient, but as described herein, other dosages may optionally also be provided). The solvent comprises ethyl lactate. In this preferred embodiment, the formulation features a solid fat, which in this Example is triglyceride (such as Tricaprin for example). The formulation also features a combination of a low HLB solvent and a high HLB solvent as described herein; for this Example, the combination comprises Polysorbate 20 and Sorbitan oleate. Preferably, the formulation features a phospholipid (in this Example, preferably lecithin). Also preferably, the formulation features an ethoxylated fat such as Cremophor for example.

TABLE 1

| Ingredient | Quantity per Capsule (mg) |
|---|---|
| Ciclosporin | 100.00 |
| Polysorbate 20 | 168.00 |
| Sorbitan oleate | 168.00 |
| Lecithin | 84.00 |
| Triglyceride | 168.00 |
| Macrogolglycerol hydroxystearate (polyoxyl 40 hydro castor oil) | 168.00 |
| Ethyl lactate | 332.00 |
| Fill weight | 1188 |

For this formulation, particle size upon mixing 1 ml of the pro-nanodispersion with 10 ml of water at body temperature was found to be 30 nm. No effect was found upon varying the pH of the water from about 2 to about 10.

Example 2

Effect of Solvent on Particle Size

An exemplary composition containing Ciclosporin, solvent, TRC (tricaprin), egg phospholipid (Avanti, USA), Tween 20, Span 80 and Cremophor was prepared with increasing amounts of ethyl lactate, as given in Table 1 (all amounts of ingredients are given in milligrams). The effect of adding increasing amounts of these ingredients to the composition of the present invention on (mean) particle size is also given in Table 2. Briefly, all compositions which contained ethyl lactate had a particle size of less than 100 nm at a temperature of 37° C. The particle size decreased as the amount of ethyl lactate was increased.

TABLE 2

Effect of Solvent on Particle Size

| Ingredient | Formulation Number | | | |
|---|---|---|---|---|
| | 1 | 2 | 3 | 4 |
| Ciclosporin | 100 | 100 | 100 | 100 |
| Ethyl lactate | 0 | 100 | 200 | 400 |
| phospholipid | 70 | 70 | 70 | 70 |
| Tween 20 | 270 | 270 | 270 | 270 |
| TRC | 130 | 130 | 130 | 130 |
| Span 80 | 100 | 100 | 100 | 100 |
| Cremophor EL | 300 | 300 | 300 | 300 |
| Particle size | 189 | 92 | 42 | 28 |

Example 3

Effect of Surfactant on Particle Size

An exemplary composition containing Ciclosporin, egg phospholipid (95% pure from Avanti, USA), ethyl lactate as a solvent, Tween 20 and Cremophor was prepared with increasing amounts of Span 80, as given in Table 3 (all amounts of ingredients are given in milligrams). The effect of adding increasing amounts of Span 80 to the composition of the present invention on (mean) particle size is also given in Table 3. Briefly, the compositions provided a liquid solution. When dispersed in deionized water at 37° C., all compositions which contained Span 80 had a particle size of less than 100 nm. The particle size decreased as the amount of Span 80 was increased.

TABLE 3

Effect of Surfactant on Particle Size

| Ingredient | Formulation Number | | | | |
|---|---|---|---|---|---|
| | 1 | 2 | 3 | 4 | 5 |
| Ciclosporin | 100 | 100 | 100 | 100 | 100 |
| Ethyl lactate | 300 | 300 | 300 | 300 | 300 |
| phospholipid | 50 | 50 | 50 | 50 | 50 |
| Tween 20 | 200 | 200 | 200 | 200 | 200 |
| Span 80 | 0 | 50 | 100 | 200 | 300 |
| Cremophor EL | 400 | 400 | 400 | 400 | 400 |
| Particle size | 155 | 88 | 54 | 32 | 28 |

Example 4

Effect of Other Ingredients on Particle Size

Different compositions containing Cyclosporin were prepared as described in Table 4 (all amounts of ingredients are given in milligrams). The effect of these ingredients on the particle size of the pro-nanodispersion solution when dispersed in warm water at 37° C. is also given in Table 4. Briefly, compositions which had both low and high HLB surfactants (such as Tween and Span) had a particle size of less than 100 nm at this temperature (which is body temperature). Tween and Cremophor can be substituted for each other as high HLB solvents (HLB>10) but a certain amount of either surfactant is required to obtain a suitable particle size, depending upon the quantities of the other components. A combination of Tween 20 and Cremophor permits the use of reduced amounts of each ingredient, as described in greater detail below. In addition, the presence of a solvent such as ethyl lactate is required. A solid fat such as tricaprin is also optional. The presence of a phospholipid is also preferred to obtain a particle size in the range of 30 nm, although the particle size remained below 100 nm even without the phospholipid as for Formulation 3, in which no phospholipid was added but the particle size was 95 nm at 37° C.

TABLE 4

Effect of Other Ingredients on Particle Size

| Ingredient | Formulation Number | | | | | | | | | |
|---|---|---|---|---|---|---|---|---|---|---|
| | 1 | 2 | 3 | 4 | 5 | 6 | 7 | 8 | 9 | 10 |
| Ciclosporin | 100 | 100 | 100 | 100 | 100 | 100 | 100 | 100 | 100 | 100 |
| Ethyl lactate | 400 | 200 | 400 | 400 | 400 | 400 | 400 | 600 | 400 | 400 |
| phospholipid | 100 | 100 | 0 | 100 | 100 | 100 | 100 | 100 | 100 | 100 |
| Tween 20 | 200 | 200 | 200 | 200 | 0 | 200 | 200 | 200 | 400 | 0 |
| TRC | 200 | 200 | 200 | 200 | 200 | 0 | 200 | 200 | 200 | 200 |
| Span 80 | 200 | 200 | 200 | 0 | 200 | 200 | 200 | 200 | 200 | 200 |
| Cremophor EL | 200 | 200 | 200 | 200 | 200 | 200 | 0 | 200 | 0 | 400 |
| Particle size | 28 | 30 | 95 | 187 | 182 | 230 | 340 | 32 | 78 | 64 |

Example 5

Storage Stability of Preferred Formulation

The composition of Example 1 was prepared at two different total quantities (all amounts of ingredients are given in milligrams), with the second quantity featuring 10-fold larger amounts of each ingredient. Both compositions were easily prepared by dissolving all components to a liquid solution by mixing with mild heating (about 40° C.). Preferably, the phospholipid was first dissolved in ethyl lactate, and then all other components were added with continuous mixing, apart from Cyclosporin which was added last. The mean particle size of the composition was measured after dispersion of different amounts of the composition in deionized water by using the light scattering technique with a Coulter N4 particle size analyzer. Both volumes of the composition had a particle size in the range of 30 nm which is preferred. This composition was used for human studies, as described in greater detail below.

The stability of the composition was tested by loading doses of 50 mg of Ciclosporin into hard gelatin capsules (size 00) or in glass containers and then storing the composition at room temperature (25° C.) or at refrigeration (4° C.). The particle size and the Ciclosporin content were determined after 3 and 6 months of storage. All samples were found to have a particle size in the range between 17.2 and 32.6 at any dispersion range (3 to 20 drops per 5 ml) when measured at a temperature of 37° C. As calculated from the peak size after analysis by HPLC (high pressure liquid chromatography), the Ciclosporin content for all stored formulations was between the required limits of 95 to 105% of the initial concentration even after 2 years of room temperature storage.

Example 6

Comparison between Sandimmune Neoral and the Present Formulation

Experiments were performed to compare the formulation of the present invention to the standard commercially available formulation for Ciclosporin (Neoral®, Novartis Inc).

The formulation of the present invention has excellent release properties as described in greater detail below. In addition, structural analyses were performed to compare the Neoral formulation with that of the present invention. These analyses showed that surprisingly the structure and behavior of the formulation of the present invention when diluted in water is very different from that of Neoral.

The following approach was taken to compare the two systems. The formulation of the present invention forms a solid nanodispersion at room temperature while Sandimmune Neoral forms an oil-in-water emulsion where the oily component is dispersed as droplets in the water phase. Without wishing to be limited by a single hypothesis, it is believed that this different behavior is related to the differences in the compositions, particular in that the formulation of this invention uses Tricaprin (a solid fat that has a melting point of 32° C.) as the hydrophobic core component of the particles, while Neoral formulations use corn oil (liquid at room temp) as the core component of the particles.

To examine these differences, the following experiments were conducted. Both concentrated formulations were dispersed in water at 25° C. with shaking and the resulted dispersions were analyzed by the following methods: confocal microscopy (Ziess Model 410 confocal scanning microscope) for visualization of the dispersion particles; particle size analysis of the dispersion by a Coulter particle size analyzer; isolation of the dispersed particles; and analysis by DSC for melting point determination of the isolated particles. Each of these is discussed in greater detail below.

Confocal Microscopy

The formulation of Example 1 was prepared with the addition of 2 mg of Nile Red as hydrophobic fluorescent marker. As a control, the nanoemulsion formulation was prepared with the addition of 2 mg Nile red using the Neoral (commercially available) formulation ingredients for the preparation of 1200 mg of formulation. The formulations were placed on a suitable slide and examined under the Confocal microscopy at room temperature. Confocal microscopy (lens #20) picture showed particles of various sizes in the range of 0.2 to 1 microns for the formulation of the present invention. In contrast the Neoral formulation did not show any particles but a continuous view which indicates the presence of a nanoemulsion.

Particle Size Analysis

Sample preparation: 0.5 ml of both formulations at a temperature in which they are in a liquid or "oily" form was added to 2 ml of double distilled water (25° C.) and hand shaken for a few seconds until mixing was uniform. The Neoral formulation formed a clear solution while the formulation of the present invention formed a milky like dispersion. In a second experiment, the formulations in oily form were dispersed in warm water (37° C.) and the dispersion was viewed by microscope. Both formulations formed almost clear solutions that do not show any particles under confocal microcopy due to its low sensitivity. The particle size of the dispersed formulation at 25° C. and at 37° C. was determined using Coulter N4 particle size analyzer.

Experimental: 0.2 ml of cyclosporin oil formulations taken from soft gelatin capsules of Neoral or the invented formulation were added to 5 ml double distilled water at 25° C. or at 37° C. and hand shaken for a few seconds to form a uniform dispersion. The dispersions were analyzed for their particle size. The formulation of the present invention showed a mean particle size of 0.5 microns with most particles in the range of 0.2 to 0.8 microns when dispersed in water at 25° C. while the Neoral formulation showed a particle size of 30.2 nanometers. The formulations at 37° C. showed a particle size of 33.6 nanometers for the formulation of the present and 32.6 nanometers for the Neoral formulation.

Ultracentrifugation of the Dispersions and DSC Analysis of the Precipitate

Experimental: Both formulations, after dispersion in deionized water at 25° C. (0.5 ml in 2 ml water with gentle shaking), were centrifuged at 20° C. for 20 minutes using 20,000 rpm centrifugation. The Neoral formulation remained clear and uniform while the formulation of the present invention separated in two layers, a solid layer and a cloudy solution. The solid precipitate was isolated by decantation and a second centrifugation took place under the following conditions: 45,000 rpm for 30 min at 20° C. A precipitate was obtained and the solution became clear. The Neoral emulsion was also centrifuged a second time under similar conditions and remained clear and homogeneous with no precipitation. This Neoral emulsion was farther centrifuged at 100,000 rpm for 30 min at 20° C.; again the emulsion remained uniform and clear.

The precipitate from the invented formulation was dried in room air over night and the pellet was analyzed by Differential Scanning Calorimeter (DSC Metler) for melting point. The melting point of the precipitate was 30.4° C. which indicates that the dispersion is a suspension of solid particles at temperatures below the melting point.

The cyclosporin formulation of the present invention forms a microdispersion, not a nanodispersion, when dispersed in water at ambient temperature (25° C.). The formed solid particles have a particle size greater than 0.2 microns, and included particles in a range of up to about 0.5 microns, with a melting point of 30° C. By contrast, the Neoral formulation formed a true nano-emulsion of oil droplet size of 30 nm at ambient temperature.

In Vitro Release

The comparative drug release rate was assessed using a dissolution apparatus test according to the USP-24 method. Both formulations achieved an in-vitro release rate of more than 90% within 15 minutes. Methods and results are described in greater detail below.

Methods

Comparison of the dissolution profiles of Ciclosporin 100 mg capsules (Dexcel, Israel) and Sandimmune Neoral 100 mg capsules (Novartis, Sweden) was carried out under the following conditions. The dissolution apparatus was a 2 paddle apparatus, containing 0.1 N HCL, containing 4 mg of lauryldimethylamine-N-oxide per ml as the dissolution medium. The capsules were dissolved in a volume of 1 liter of the dissolution medium, at a temperature of 37° C. and a rotation speed of 75 rpm. At various time points (0 min, 15 min, 30 min and 60 min), samples were withdrawn from the dissolution apparatus and were assayed with an HPLC apparatus to determine the level of ciclosporin in the sample. A standard, prepared by adding 50 mg of cyclosporine to 30 ml of ethanol and then diluting 10 ml of the resultant solution with 40 ml of the dissolution medium, was used to calibrate the HPLC results. The mobile phase featured a mixture of 0.05 M phosphoric acid and tetrahydrofuran, at a ratio of 59:41 volume per volume.

Results

Table 6 shows the amount of ciclosporin released from each formulation at the various timepoints.

TABLE 6 comparison of release rates

| | Dissolved value (%) | |
|---|---|---|
| Time (min) | B.N. 161200 Dexcel | B.N. C43 Novartis |
| 0 | 0 | 0 |
| 15 | 103 | 90 |
| 30 | 103 | 96 |
| 60 | 103 | 97 |

Figure 1:
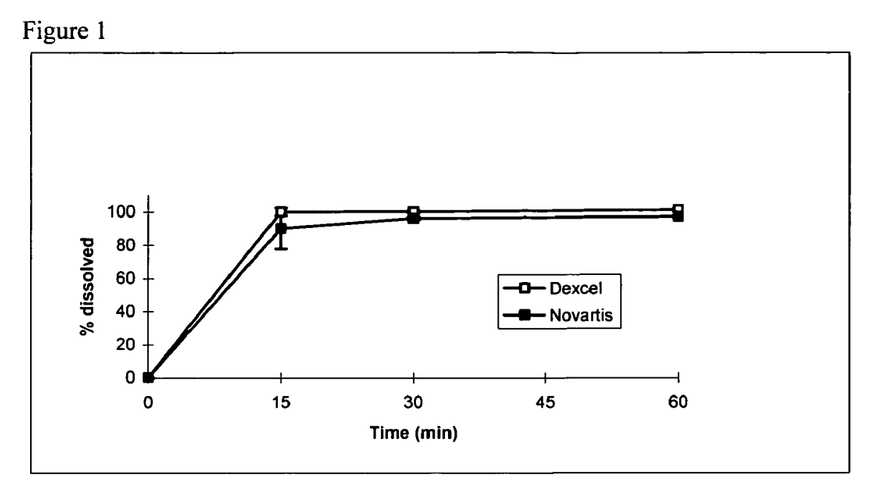

Similarly to Table 6, FIG. 1 shows the mean percent of drug (CsA) released versus time for test (Deximune®) (□) and reference Neoral® 100 mg (■) using USP 24 method. Both test and reference products exhibited very similar dissolution profiles. Both formulations showed a very fast release rate with more than 90% of the drug released and dissolved within 15 minutes (FIG. 1). The release rates for both formulations were superimposable.

Example 7

Analysis of Preferred Formulation

In Vitro Activity

The composition of Example 5 was prepared 5 times independently for 400 mg Ciclosporin. The particle size, Ciclosporin content, the morphology of the formed particles and the melting point of the particles was determined. The bioactivity of the Ciclosporin formulation on T-cells was also determined.

The particle size of all formulations ranged between 18 to 29 nm when dispersed in deionized water or 0.1 N HCl solution. The particles were viewed by Transmission Electron Microscope (TEM) at high magnification. Spherical particles with a narrow size distribution in the range of 30 nm were observed. The melting point of the particles was determined by differential scanning calorimeter (DSC) and was found to be in a temperature range of from 30 to 35 C. The composition was highly effective at inhibiting the activity of T-cells. The results clearly indicate the superior stability, reproducibility and efficacy of the preferred formulation.

Example 8

Pharmacokinetic Human Studies

A randomized pilot pharmacokinetic study was undertaken to investigate the pharmacokinetic performance of the composition of the present invention, when compared to the standard commercially available formulation for Ciclosporin (Neoral®, Novartis Inc).

The investigation was designed as a randomized, open-labeled, two-period, two-treatment crossover study, in 24 healthy fasted male volunteers. The subjects were administered a single 200 mg cyclosporine (CsA) dose of either formulation. The formulation according to the present invention that was tested is given in Example 1.

Serial venous blood samples were obtained over 24 hours after each administration to measure cyclosporin concentrations in the blood. For both treatments, a mean maximum blood concentration (Cmax) of approximately 1200 ng/ml was obtained at about 1.6 hours (tmax) after administration; the area under the blood concentration-time curve (AUC) was, on average, 4900 ng×hr/ml.

As a summary of these results, bioequivalence was conclusively demonstrated for both rate (Cmax and tmax) and extent (AUC) of CsA absorption, between the two treatments.

The point estimates and its 90% confidence intervals were within the respective equivalence ranges for the pharmacokinetic parameters and were included in the range for narrow therapeutic drugs index.

Methods and results are discussed in more detail below.

Methods

In Vivo Bioequivalence Study

The study was performed with twenty-four healthy male volunteers who all started and completed the study.

The study protocol was a randomized, two-treatment, two-period, crossover investigation with a washout phase of one week between the two study periods. The treatments consisted of a single oral 200 mg dose (2×100 mg soft gelatin capsules) with 240 ml water.

Subjects were confined to the study center from 10-12 hours before until 24 hours after each drug administration. On the days of drug administration, they fasted for 12 hours before dosing until 4 hours after dosing. Thereafter they were given standard, scheduled meals that were identical on both dosing days. The time of day of drug intake was identical for a given subject for each dosing. Fluid intake was also standard, and no alcohol or xanthines were allowed during the periods of confinements. Study participants were asked to refrain from the use of all drugs, including over-the-counter medications, for at least 2 weeks before the first administration, as well as during the entire study. After each administration, venous blood samples to determine cyclosporin in whole blood were obtained before and then 0.25, 0.5, 0.75, 1, 1.5, 2, 2.5, 3, 3.5, 4, 4.5, 5, 6, 9, 12, 15 and 24 hours after dosing. Samples were collected in EDTA-containing tubes, gently inverted several times. Two whole blood aliquots were immediately frozen at −36° C.

The following bioanalytical method was used to analyze the level of Cyclosporin in the blood samples. Blood analysis was performed by a pre-validated method of Fluorescence Polarization Immunoassay—TDx, with TDx/TDxFLx cyclosporin monoclonal whole blood assay kits (Abbott Laboratories), for the determination of drug plasma concentrations having an LOQ of 50 ng/ml. The assay was used according to manufacturer instructions.

Statistical Analysis

Parametric general linear model procedures are recommended for the analysis of pharmacokinetic data derived from in vivo bioequivalence studies. An analysis of variance (ANOVA) was performed on the pharmacokinetic parameters AUC and Cmax, after logarithmic transformation using General Linear Models (GLM) procedures of SAS program. Appropriate statistical models pertaining to the design of the bioequivalence study were employed.

The two one-sided hypotheses at the 5% level of significance were tested for AUC and Cmax, by constructing the 90% confidence intervals for the ratio between the test and reference averages. The range for concluding bioequivalence (AUC, Cmax) was set to 80%-125% using the logarithmically transformed data and the Tmax was evaluated by using the nonparametric analysis for the median difference were computed, all based on the EU and FDA guidelines.

All statistical computations were performed by the SAS software version 8.0, Cary, N.C., USA.

Results and Discussion

Figure 2:
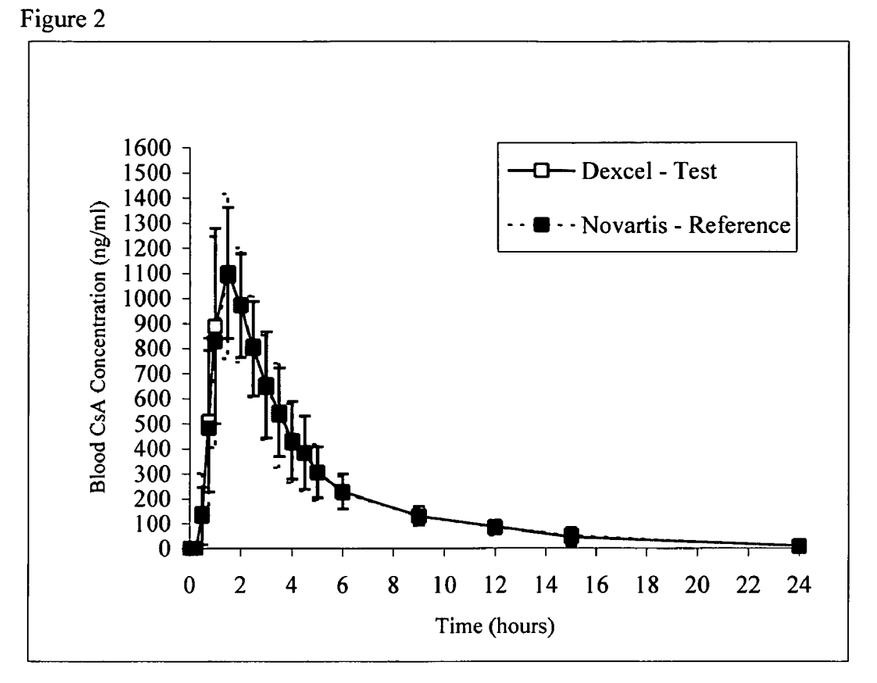

FIG. 2 shows the mean CsA concentration-time profiles after single oral administration of 200 mg of the drug given as soft gelatin capsules test (□) (Dexcel Ltd.) reference (Novartis Inc.) (■) to 24 healthy volunteers.

Superimposable blood CsA concentration profiles were obtained and the mean relative bioavailability of Dexcel's formulation compared with that of Neoral® was 101%.

The values for the main pharmacokinetic measures and pertinent information on the calculation are summarized in Table 7 below.

Therefore, it was concluded that these oral CsA formulations are bioequivalent

This human study clearly indicates the efficacy of the formulation of the present invention as compared to the best commercially available formulation. Sandimmun Neoral® (Novartis Inc.).

Example 9

Opthalmic Topical Cyclosporin Formulation

Effective topical administration of Cyclosporin A to the eye would reduce or eliminate to a large extent the systemic side effects by restricting activity to the locus of the condition being treated. Several formulations for topical delivery of cyclosporine have been reported, as described for example U.S. Pat. No. 4,649,047 and U.S. Pat. No. 6,582,718. However, the utility and effectiveness of Cyclosporin A in treating diseases and conditions of the eye has been hindered until now by the lack of suitable eye-drops which are adapted to the delicate nature of the eye. Eye-drops should not cause patient discomfort and should also permit a convenient administration regimen, by not requiring frequent administration, while providing adequate drug substance delivery to the external and internal regions of the eye. A further difficulty is the very poor solubility of cyclosporin A in water, which frequently leads to precipitation of cyclosporin A from aqueous-based eye-drops, causing major irritation of the eye.

There is thus an urgent need to develop a topical, ophthalmic formulation which causes less irritation to the eyes, is

TABLE 7

| N = 24 | Pharmacokinetic Parameters | | | | |
|---|---|---|---|---|---|
| | $AUC_{(0-\infty)}$ (ng × hour/ml) | $AUC_{(0-t)}$ (ng × hour/ml) | Cmax (ng/ml) | Tmax (hours) | T½ (hours) |
| Deximune ® (Dexcel) | | | | | |
| Mean ± SD | 4930 ± 1283 | 4418 ± 1153 | 1184 ± 215 | 1.65 ± 0.48 | 5.9 ± 2.42 |
| Neoral ® (Novartis) | | | | | |
| Mean ± SD | 4866 ± 1107 | 4345 ± 998 | 1203 ± 231 | 1.63 ± 0.52 | 6.05 ± 2.48 |
| Point Estimate (Ratio)* | 101 | 101 | 99 | | |
| 90% ANOVA C.I. | | | | | |
| Lower Limit | 93 | 93 | 90 | | |
| Upper Limit | 109 | 110 | 109 | | |
| Median Difference | | | | 0.00 | 0.05 |
| Minimum | | | | −1.50 | −5.21 |
| Maximum | | | | 1.50 | 8.41 |
| 90% Non-Parametric C.I. | | | | | |
| Lower Limit | | | | −0.25 | −0.99 |
| Upper Limit | | | | 0.25 | 0.26 |

*The presented ratios expressed in percentage (%) are geometric means of the individual ratios between test and reference parameters. Parametric estimators and 90% Parametric Confidence Intervals, based on the linear model with logarithmic transformation, are brought.

better adapted to evenly distribute cyclosporin A in the eyes and does not cause precipitation of cyclosporin. Also, a stable formulation of cyclosporine that remains in an anhydrous (dried) in storage, while still being capable of dispersion into a nanoparticulate formulation shortly prior to administration, is preferred. Such formulation can be mixed with water to form a nanodispersion which is stable for a few weeks of the treatment.

According to preferred embodiments thereof, the formulations of the present invention can be mixed with a sterile aqueous medium that is suitable for eye drops to form a solution featuring 0.01 to 10 mg/ml of cyclosporin as active agent after dilution in saline prior to use with a particle size of less than 100 nanometers at body temperature but with a particle size of at least about 150 nm at room temperature. These clear diluted dispersions can optionally be administered in the eye with a conventional eye dropper. The formulation is optionally and preferably stored as pro-nanodispersion in the bottle while at the time of initial treatment, the pro-nanodispersion oily formulation is diluted with isotonic sterile buffered solution to form a concentration of 1 mg/ml to about 0.01 mg/ml. These dispersions are stable for at least a few weeks. Furthermore, they require little or no preservative as the formulation is preferably mixed with water shortly before use. This also increases the stability of the drug.

Alternatively, the pro-nanodispersion is pre-mixed with the buffer solution and packed in single use vesicles or in a multidose bottle which may contain benzyl alcohol or chloramphenicol as preservative. Non-limiting examples of preservatives with suitable amounts (optionally ranges) include benzalkonium chloride, 0.004-0.01%; edetate sodium 0.02-0.05%; Phenylmercuric acetate or Phenylmercuric nitrate 0.002%; and/or Chlorobutanol and Benzyl alcohol 0.5% (pH should be buffered to 5.0-5.5)

According to preferred embodiments of the present invention, a preferred formulation features cyclosporin in a pro-nanodispersion system comprising polysorbate-20 and polyoxyl 40 hydrogenated castor oil that are approved for ophthalmic solutions. Sorbitan monooleate is considered as safe for eye formulations ("Handbook of Pharmaceutical Excipients", 4th edition, 2003), while lecithin and solid triglyceride are considered as safe for use in ophthalmic formulations. The solvent ethyl lactate is considered to be safe, as ethyl lactate is a food additive although it has not been used yet in eye formulations.

According to preferred embodiments of the present invention, the ophthalmic compositions are preferably formulated as pro-nanodispersions, which upon mixing with saline suitable for eye drop formulations, form a nanodispersion. With these ophthalmic compositions, very good therapeutic results may be obtained even when the cyclosporin is present in low concentrations; for example within the range of from about 0.01 to about 1.0% (w/v), preferably about 0.1% (w/v).

In a typical formulation, Cyclosporin is preferred as the active ingredient (this Example includes 100 mg of the active ingredient, but as described herein, other dosages may optionally also be provided). The solvent preferably comprises ethyl lactate, but may optionally comprise N-C1-4 alkyl pyrrolidone, optionally and preferably N-methylpyrrolidone, used in a similar amount as for ethyl lactate. The formulation may optionally and preferably comprise a solid fat, which in this Example is a solid triglyceride (such as Tricaprin or trilaurin for example). The formulation also features a combination of a low HLB solvent and a high HLB solvent as described herein; for this Example, the combination comprises Polysorbate 20 and Sorbitan oleate. Preferably, the formulation features a phospholipid (in this Example, preferably lecithin). Also preferably, the formulation features an ethoxylated fat such as Cremophor for example. The different examples of ingredients previously described in the specification may also optionally be used for the ophthalmic formulation, as long as the ingredients are specially formulated for use in the eye (and/or are otherwise approved for use in the eye).

Exemplary ranges of amounts of different materials are given in Table 8 below as milligrams of material per 10 ml of formulation (the amount in parentheses is for mg per ml formulation).

TABLE 8 range of components of the eye formulation

| Ingredient | Quantity per 10 ml 0.1% cyclosporine final formulation (mg) preferred range |
|---|---|
| Ciclosporin | 10.00 mg (within the range of from about 0.01 to about 1.0% (w/v), preferably about 0.1% (w/v)) |
| Hydrophilic surfactant (Polysorbate 20) | From about 3 to about 40 (from about 0.3 to about 4.0) |
| Hydrophobic surfactant (Sorbitan oleate) | From about 3 to about 40 (from about 0.3 to about 4.0) |
| Phospholipid (lecithin) | From about 1 to about 20 (from about 0.1 to about 2.0) |
| Solid fat (tricaprin, ethyl stearate) | From about 3 to about 30 (from about 0.3 to about 3.0) |
| Macrogolglycerol hydroxystearate (polyoxyl 40 hydro castor oil, Cremophor; or any ethoxylated fat) | From about 1 to about 20 (from about 0.1 to about 2.0) |
| Ethyl lactate or N-methyl pyrrolidone | From about 3 to about 30 (from about 0.3 to about 3.0) |
| Saline for eye drops | 10 ml |

The amount of each component is preferably determined according to the amounts of the other components. For example, reducing the amount of hydrophilic surfactant (Polysorbate 20) may require increasing the amount of Cremophor.

Table 9 shows an exemplary optical formulation according to the present invention.

TABLE 9

| Ingredient | Quantity per 10 ml (mg) |
|---|---|
| Ciclosporin | 10.00 |
| Polysorbate 20 | 16.80 |
| Sorbitan oleate | 16.80 |
| Lecithin | 8.40 |
| Triglyceride | 16.80 |
| Macrogolglycerol hydroxystearate (polyoxyl 40 hydro castor oil) | 10.00 |
| Ethyl lactate | 10.00 |
| Saline for eye drops | 10 ml |

For this illustrative, non-limiting formulation, particle size upon mixing 100 mg of the pro-nanodispersion with 10 ml of water at body temperature was found to be less than 200 nm. This pro-nanodispersion formulation is stable for more than one year when kept at room temperature in a sealed glass vial. Prior to use, the bottle is opened and 10 ml saline for eye drops is added and shaken gently to form immediately a translucent dispersion which does not cause irritation to the eye.

Experimental Example

A diluted formulation of 0.1 mg/ml of the formulation described above was instilled in rabbit eye for 4 hours every 30 minutes and the eye was inspected for any adverse effects. No adverse effects were noted immediately or at one week post instillation.

Example 10

Methods of Administration of Cyclosporins

A cyclosporin, such as Ciclosporin, can be administered to a subject in a number of ways, which are well known in the art. Hereinafter, the term "subject" refers to the human or lower animal to whom cyclosporin was administered. For example administration may be done topically (including ophtalmically, vaginally, rectally, intranasally), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. An optional but preferred formulation for administration as eye drops is described above.

Compositions for oral administration include powders or granules, suspensions or solutions in water or non-aqueous media, sachets, capsules or tablets. Thickeners, diluents, flavorings, dispersing aids, emulsifiers or binders may be desirable. Compositions for oral administration preferably include a soft or hard gelatin capsule.

Formulations for parenteral administration may include but are not limited to sterile aqueous solutions which may also contain buffers, diluents and other suitable additives.

The formulations of the present invention may optionally be administered as a pro-nanodispersion or as a nanodispersion in aqueous liquid. Alternatively, these formulations may be lyophilized (dried) after the formation of the nanodispersion in aqueous liquid. The lyophilized (dried) dispersion is also optionally administered to the subject. The preferred route of administration is oral administration.

Dosing is dependent on the severity of the symptoms and on the responsiveness of the subject to cyclosporin. Persons of ordinary skill in the art can easily determine optimum dosages, dosing methodologies and repetition rates.

Example 11

Methods of Treatment with Cyclosporins

Cyclosporins are particularly noted for the treatment and prevention of organ or tissue transplant rejection, for the treatment and prevention of autoimmune disease and of inflammatory conditions, and for the treatment of multi-drug resistance (MDR).

With regard to the treatment and prevention of organ or tissue transplant rejection, the compositions of the present invention containing cyclosporin are useful for the treatment of the recipients of heart, lung, combined heart-lung, liver, kidney, pancreatic, bone-marrow, skin or corneal transplants, and in particular allogenic transplants, for example. In addition, the compositions of the present invention are useful for the prevention of graft-versus-host-disease, which can sometimes be seen following bone marrow transplantation.

With regard to the treatment and prevention of autoimmune disease and of inflammatory conditions, the compositions of the present invention containing cyclosporin may be useful for the treatment of autoimmune hematological disorder (including hemolytic anemia, aplastic anemia pure red cell anemia and idiopathic thrombocytopenia), systemic lupus erythematosus, polychondritis, scleroderma, Wegener granulamatosis, dermatomyositis, chronic active hepatitis, myasthenia gravis, psoriasis, Steven-Johnson syndrome, idiopathic sprue, autoimmune inflammatory bowel disease (such as ulcerative colitis and Crohn's disease), endocrine opthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, such as idiopathic nephrotic syndrome or minimal change nephropathy).

In addition, these compositions may be particularly useful for inflammatory conditions with an etiology including an autoimmune component such as arthritis (for example. rheumatoid arthritis, arthritis chronica progrediente and arthritis deformans) and rheumatic diseases.

With regard to multi-drug resistance (MDR), the compositions of the present invention containing cyclosporin may be useful for reversing or abrogating anti-neoplastic agent resistance in tumors and the like. The following examples are illustrations only of methods of treating these disorders with the compositions of the present invention containing cyclosporin, and are not intended to be limiting. The method includes the step of administering the composition of the present invention containing cyclosporin, as described in above, to a subject to be treated. The composition of the present invention is administered according to an effective dosing methodology, preferably until a predefined endpoint is reached (if possible), such as the absence of symptoms of the disorder in the subject. For other disorders, such as organ or tissue transplant rejection, the composition of the present invention may need to be administered continuously without any endpoint.

Hereinafter, the term "treatment" includes both pretreatment, before a pathological condition has arisen, and treatment after the condition has arisen. The term "treating" includes both treating the subject after the pathological condition has arisen, and preventing the development of the pathological condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composition for administering a cyclosporin compound, the composition comprising: (a) a pro-nanodispersion comprising: (i) a solid fat; (ii) ethyl lactate; (iii) at least two surfactants comprising a low HLB surfactant and a high HLB surfactant, wherein a difference between the HLB values for said low and said high HLB surfactants is at least about 5 units; and (iv) an ethoxylated fat; (b) a pharmaceutically effective amount of the cyclosporin compound; and a suitable diluent for administration to the eye.

2. The formulation of claim 1, wherein said cyclosporine is present in an amount of from about 0.01 to about 1.0% (w/v).

3. The formulation of claim 2, wherein said cyclosporine is present in an amount of about 0.1% (w/v).

4. The formulation of claim 1, wherein said low HLB surfactant comprises sorbitan oleate.

5. The formulation of claim 4, wherein said sorbitan oleate is present in an amount of from about 0.3 to about 4 mg per ml of the final formulation.

6. The formulation of claim 1, wherein said solid fat comprises tricaprin or ethyl stearate, or a combination thereof.

7. The formulation of claim 6, wherein said solid fat comprises tricaprin.

8. The formulation of claim 7, wherein said tricaprin is present in an amount of from about 0.3 to about 3 mg per ml of the final formulation.

9. The formulation of claim 1, wherein said ethyoxylated fat comprises macrogolglycerol hydroxystearate.

10. The formulation of claim 9, wherein said macrogolglycerol hydroxystearate is present in an amount of from about 0.1 to about 2 mg per ml of the final formulation.

11. The formulation of claim 1, further comprising: a phospholipid.

12. The formulation of claim 11, wherein said phospholipid comprises lecithin.

13. The formulation of claim 12, wherein said lecithin is present in an amount of from about 0.1 to about 2 mg per ml of the final formulation.

* * * * *